US011110288B2

United States Patent
Kaib

(10) Patent No.: US 11,110,288 B2
(45) Date of Patent: Sep. 7, 2021

(54) SYSTEMS AND METHODS FOR CONFIGURING A WEARABLE MEDICAL MONITORING AND/OR TREATMENT DEVICE

(71) Applicant: ZOLL Medical Corporation, Chelmsford, MA (US)

(72) Inventor: Thomas E. Kaib, North Huntingdon, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 3 days.

(21) Appl. No.: 15/841,705

(22) Filed: Dec. 14, 2017

(65) Prior Publication Data

US 2018/0117348 A1 May 3, 2018

Related U.S. Application Data

(62) Division of application No. 13/782,232, filed on Mar. 1, 2013, now Pat. No. 9,878,171.

(Continued)

(51) Int. Cl.
*A61N 1/39* (2006.01)
*G16H 40/40* (2018.01)
(Continued)

(52) U.S. Cl.
CPC .......... *A61N 1/3931* (2013.01); *G16H 20/30* (2018.01); *G16H 40/40* (2018.01); *G16H 40/63* (2018.01);
(Continued)

(58) Field of Classification Search
None
See application file for complete search history.

(56) References Cited

U.S. PATENT DOCUMENTS 3,534,727 A 10/1970 Roman
3,553,651 A 1/1971 Bird et al.
(Continued)

FOREIGN PATENT DOCUMENTS

EP 1642616 A2 4/2006
EP 1455640 B1 1/2008
(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.
(Continued)

*Primary Examiner* — Michael W Kahelin
*Assistant Examiner* — Elizabeth K So
(74) *Attorney, Agent, or Firm* — Finch & Maloney PLLC

(57) ABSTRACT

A system including an ambulatory medical treatment device is provided. The ambulatory medical treatment device includes a memory, a treatment component configured to treat a patient, at least one processor coupled to the memory and the treatment component, a user interface component, and a system interface component. The user interface component is configured to receive an update session request and to generate the update session identifier responsive to receiving the request. The system interface component is configured to receive an encoded request including an identifier of an update session and device update information, to decode the encoded request to generate a decoded request including the device update information and the identifier of the update session, to validate the decoded request by determining that the update session identifier matches the identifier of the update session, and to apply the device update information to the ambulatory medical treatment device.

29 Claims, 15 Drawing Sheets

Related U.S. Application Data

(60) Provisional application No. 61/606,248, filed on Mar. 2, 2012.

(51) Int. Cl.
*G16H 40/63* (2018.01)
*G16H 20/30* (2018.01)
*G16H 40/67* (2018.01)
*G16H 80/00* (2018.01)

(52) U.S. Cl.
CPC ............. *G16H 40/67* (2018.01); *G16H 80/00* (2018.01); *A61N 1/3925* (2013.01)

(56) References Cited

U.S. PATENT DOCUMENTS

| | | | |
|---|---|---|---|
| 4,094,310 A | 6/1978 | McEachern et al. | |
| 4,136,690 A | 1/1979 | Anderson et al. | |
| 4,422,459 A | 12/1983 | Simson | |
| 4,458,691 A | 7/1984 | Netravali | |
| 4,632,122 A | 12/1986 | Johansson et al. | |
| 4,928,690 A | 5/1990 | Heilman et al. | |
| 4,991,217 A | 2/1991 | Garrett et al. | |
| 5,000,189 A | 3/1991 | Throne et al. | |
| 5,062,834 A | 11/1991 | Gross et al. | |
| 5,078,134 A | 1/1992 | Heilman et al. | |
| 5,243,978 A | 9/1993 | Duffin, Jr. | |
| 5,330,505 A | 7/1994 | Cohen | |
| 5,342,404 A | 8/1994 | Alt et al. | |
| 5,348,008 A | 9/1994 | Bomn et al. | |
| 5,357,696 A | 10/1994 | Gray et al. | |
| 5,381,798 A | 1/1995 | Burrows | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,827,196 A | 10/1998 | Yeo et al. | |
| 5,887,978 A | 3/1999 | Lunghofer et al. | |
| 5,924,979 A | 7/1999 | Swedlow et al. | |
| 5,929,601 A | 7/1999 | Kaib et al. | |
| 5,944,669 A | 8/1999 | Kaib | |
| 6,016,445 A | 1/2000 | Baura | |
| 6,045,503 A | 4/2000 | Grabner et al. | |
| 6,047,203 A | 4/2000 | Sackner et al. | |
| 6,065,154 A | 5/2000 | Hulings et al. | |
| 6,097,987 A | 8/2000 | Milani | |
| 6,148,233 A | 11/2000 | Owen et al. | |
| 6,169,387 B1 | 1/2001 | Kaib | |
| 6,253,099 B1 | 6/2001 | Oskin et al. | |
| 6,280,461 B1 | 8/2001 | Glegyak et al. | |
| 6,406,426 B1 | 6/2002 | Reuss et al. | |
| 6,546,285 B1 | 4/2003 | Owen et al. | |
| 6,681,003 B2 | 1/2004 | Linder et al. | |
| 6,690,969 B2 | 2/2004 | Bystrom et al. | |
| 6,804,554 B2 | 10/2004 | Ujhelyi et al. | |
| 6,827,695 B2 | 12/2004 | Palazzolo et al. | |
| 6,865,413 B2 | 3/2005 | Halperin et al. | |
| 6,908,437 B2 | 6/2005 | Bardy | |
| 6,961,612 B2 | 11/2005 | Elghazzawi et al. | |
| 6,990,373 B2 | 1/2006 | Jayne et al. | |
| 7,074,199 B2 | 7/2006 | Halperin et al. | |
| 7,108,665 B2 | 9/2006 | Halperin et al. | |
| 7,118,542 B2 | 10/2006 | Palazzolo et al. | |
| 7,122,014 B2 | 10/2006 | Palazzolo et al. | |
| 7,149,579 B1 | 12/2006 | Koh et al. | |
| 7,220,235 B2 | 5/2007 | Geheb et al. | |
| 7,295,871 B2 | 11/2007 | Halperin et al. | |
| 7,340,296 B2 | 3/2008 | Stahmann et al. | |
| 7,453,354 B2 | 11/2008 | Reiter et al. | |
| 7,476,206 B2 | 1/2009 | Palazzolo et al. | |
| 7,488,293 B2 | 2/2009 | Marcovecchio et al. | |
| 7,712,373 B2 | 5/2010 | Nagle et al. | |
| 7,831,303 B2 | 11/2010 | Rueter et al. | |
| 7,974,689 B2 | 7/2011 | Volpe et al. | |
| 7,991,460 B2 | 8/2011 | Fischell et al. | |
| 8,121,683 B2 | 2/2012 | Bucher et al. | |
| 8,140,154 B2 | 3/2012 | Donnelly et al. | |
| 2003/0004547 A1 | 1/2003 | Owen et al. | |
| 2003/0032988 A1 | 2/2003 | Fincke | |
| 2003/0095648 A1 | 5/2003 | Kaib et al. | |
| 2003/0109904 A1 | 6/2003 | Silver et al. | |
| 2003/0149462 A1 | 8/2003 | White et al. | |
| 2003/0158593 A1 | 8/2003 | Heilman et al. | |
| 2003/0174049 A1 | 9/2003 | Beigel et al. | |
| 2003/0195567 A1 | 10/2003 | Jayne et al. | |
| 2003/0212311 A1 | 11/2003 | Nova et al. | |
| 2004/0007970 A1 | 1/2004 | Ma et al. | |
| 2004/0049233 A1 | 3/2004 | Edwards | |
| 2004/0143297 A1 | 7/2004 | Ramsey | |
| 2004/0162510 A1 | 8/2004 | Jayne et al. | |
| 2004/0215247 A1* | 10/2004 | Bolz ........................ A61N 1/39 607/7 |
| 2004/0249419 A1 | 12/2004 | Chapman et al. | |
| 2005/0049515 A1 | 3/2005 | Misczynski et al. | |
| 2005/0131465 A1 | 6/2005 | Freeman et al. | |
| 2005/0144043 A1 | 6/2005 | Holland et al. | |
| 2005/0246199 A1 | 11/2005 | Futch | |
| 2005/0283198 A1 | 12/2005 | Haubrich et al. | |
| 2006/0036292 A1 | 2/2006 | Smith et al. | |
| 2006/0085049 A1 | 4/2006 | Cory et al. | |
| 2006/0095091 A1 | 5/2006 | Drew | |
| 2006/0155589 A1* | 7/2006 | Lane .................... A61B 5/0002 705/4 |
| 2006/0178706 A1 | 8/2006 | Lisogurski et al. | |
| 2006/0211934 A1 | 9/2006 | Hassonjee et al. | |
| 2006/0220809 A1 | 10/2006 | Stigall et al. | |
| 2006/0264776 A1 | 11/2006 | Stahmann et al. | |
| 2006/0270952 A1 | 11/2006 | Freeman et al. | |
| 2007/0073120 A1 | 3/2007 | Li et al. | |
| 2007/0118056 A1 | 5/2007 | Wang et al. | |
| 2007/0129769 A1 | 6/2007 | Bourget et al. | |
| 2007/0143864 A1 | 6/2007 | Cabana et al. | |
| 2007/0161913 A1 | 7/2007 | Farrell et al. | |
| 2007/0169364 A1 | 7/2007 | Townsend et al. | |
| 2007/0196320 A1 | 8/2007 | Yasin | |
| 2007/0197878 A1 | 8/2007 | Shklarksi | |
| 2007/0239214 A1 | 10/2007 | Cinbis | |
| 2007/0239220 A1 | 10/2007 | Greenhut et al. | |
| 2007/0265671 A1 | 11/2007 | Roberts et al. | |
| 2008/0021532 A1 | 1/2008 | Kveen et al. | |
| 2008/0030656 A1 | 2/2008 | Watson et al. | |
| 2008/0031270 A1 | 2/2008 | Tran et al. | |
| 2008/0033495 A1 | 2/2008 | Kumar | |
| 2008/0045815 A1 | 2/2008 | Derchak et al. | |
| 2008/0058884 A1 | 3/2008 | Matos | |
| 2008/0097793 A1 | 4/2008 | Dicks et al. | |
| 2008/0103402 A1 | 5/2008 | Stickney et al. | |
| 2008/0167535 A1 | 7/2008 | Stivoric et al. | |
| 2008/0177341 A1 | 7/2008 | Bowers | |
| 2008/0183090 A1 | 7/2008 | Farringdon et al. | |
| 2008/0249591 A1 | 10/2008 | Gaw et al. | |
| 2008/0287749 A1 | 11/2008 | Reuter | |
| 2008/0294019 A1 | 11/2008 | Tran | |
| 2008/0306562 A1 | 12/2008 | Donnelly et al. | |
| 2008/0312520 A1 | 12/2008 | Rowlandson et al. | |
| 2008/0312522 A1 | 12/2008 | Rowlandson et al. | |
| 2009/0018428 A1 | 1/2009 | Dias et al. | |
| 2009/0066366 A1 | 3/2009 | Solomon | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076405 A1 | 3/2009 | Amurthur et al. | |

(56) References Cited

U.S. PATENT DOCUMENTS

| | | |
|---|---|---|
| 2009/0076559 A1 | 3/2009 | Libbus et al. |
| 2009/0093687 A1 | 4/2009 | Telfort et al. |
| 2009/0118808 A1 | 5/2009 | Belacazar et al. |
| 2009/0138059 A1 | 5/2009 | Ouwerkerk |
| 2009/0146822 A1 | 6/2009 | Soliman |
| 2009/0212984 A1 | 8/2009 | Baker |
| 2009/0231124 A1 | 9/2009 | Klabunde et al. |
| 2009/0232286 A1 | 9/2009 | Hurwitz |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0318779 A1 | 12/2009 | Tran |
| 2010/0010559 A1 | 1/2010 | Zhang et al. |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0081962 A1 | 4/2010 | Hamaguchi et al. |
| 2010/0114243 A1 | 5/2010 | Nowak et al. |
| 2010/0171611 A1 | 7/2010 | Gao et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0015533 A1 | 1/2011 | Cox et al. |
| 2011/0022105 A9 | 1/2011 | Owen et al. |
| 2011/0093840 A1 | 4/2011 | Pynenburg et al. |
| 2011/0098765 A1 | 4/2011 | Patel |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0053479 A1 | 3/2012 | Hopenfeld |

FOREIGN PATENT DOCUMENTS

| | | |
|---|---|---|
| EP | 1720446 B1 | 7/2010 |
| JP | H11-149379 A | 6/1999 |
| JP | 2002-514107 A | 5/2002 |
| JP | 2002200059 A | 7/2002 |
| JP | 2004-318839 A | 11/2004 |
| JP | 2009-521865 A | 6/2009 |
| JP | 2009-528909 A | 8/2009 |
| JP | 2012-003311 A | 1/2012 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2007019325 A2 | 2/2007 |
| WO | 2009034506 A1 | 3/2009 |
| WO | 2009122277 A2 | 10/2009 |
| WO | 2010025432 A1 | 3/2010 |
| WO | 2010077997 A2 | 7/2010 |
| WO | 2012006524 A1 | 1/2012 |

OTHER PUBLICATIONS

Association for the Advancement of Medical Instrumentation, ANSI/AAMI DF80:2003 "Medical Electrical Equipment—Part 2-4: Particular Requirements for the Safety of Cardiac Defibrillators (including Automated External Defibrillators)", 2004, ISBN 1-57020-210-9; abstract; p. vi, p. 50, section 107.1.2.

DeBock et al., "Captopril Treatment of Chronic Heart Failure in the Very Old", J. Gerontol, (1994) 49: M148-M152.

International Search Report and Written Opinion from PCT/US2013/028598 dated May 9, 2013.

O'Keefe et al., "Reproducibility and Responsiveness of Quality of the Assessment and Six Minute Walk Test in Elderly Heart Failure Patients", Heart (1998) 80: 377-382.

Extended European Search Report dated Dec. 18, 2015 for EP Application No. 13755470.5, 6 pages.

* cited by examiner

SYSTEMS AND METHODS FOR CONFIGURING A WEARABLE MEDICAL MONITORING AND/OR TREATMENT DEVICE

CROSS-REFERENCE TO RELATED APPLICATIONS

This application claims benefit under 35 U.S.C. § 121 as a division of U.S. patent application Ser. No. 13/782,232, filed Mar. 1, 2013, now U.S. Pat. No. 9,878,171, titled "SYSTEMS AND METHODS FOR CONFIGURING A WEARABLE MEDICAL MONITORING AND/OR TREATMENT DEVICE." U.S. patent application Ser. No. 13/782,232 claims benefit under 35 U.S.C. § 119(e) to U.S. Provisional Application Ser. No. 61/606,248, filed Mar. 2, 2012, titled "SYSTEMS AND METHODS FOR CONFIGURING A WEARABLE MEDICAL MONITORING AND/OR TREATMENT DEVICE." Each of these related applications is hereby incorporated herein by reference in its entirety.

U.S. patent application Ser. No. 12/833,173, now U.S. Pat. No. 8,140,154, titled "Wearable Medical Treatment Device," filed on Jul. 9, 2010 is hereby incorporated herein by reference in its entirety. This specification further incorporates by reference, in their entirety, U.S. Pat. Nos. 4,928,690; 6,065,154; 5,944,669; 5,741,306; 6,681,003; 6,253,099; and 5,078,134.

NOTICE OF MATERIAL SUBJECT TO COPYRIGHT PROTECTION

Portions of the material in this patent document are subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of Invention

At least one embodiment of the present invention relates generally to a wearable therapeutic device, and more specifically, to a wearable therapeutic device configured to monitor or treat a subject.

2. Discussion of Related Art

Heart failure and other chronic conditions are a major health concern worldwide. Heart failure is a progressive disease with varying symptoms such as fatigue, coughing, diminished exercise capacity, shortness of breath, fluid retention, swelling in the abdomen or legs, lung congestion, and cardiac arrhythmias. Heart failure can be treated, and its symptoms mitigated, by lifestyle modifications, medications, surgical procedures such as heart transplants, and mechanical therapies. These efforts can come with side effects and limited success rates. Heart failure continues to reduce the quality of life of victims.

SUMMARY OF THE INVENTION

Aspects and embodiments of the present invention are directed to a wearable therapeutic and monitoring treatment device. The device monitors and collects health related information from the subject, and uses this information to determine if treatment is warranted, to suggest lifestyle modifications, and to adjust treatment regimens. The device can further include an external defibrillator to apply treatment such as defibrillation to the subject when necessary. By monitoring a subject's conditions in a nearly continuous fashion in essentially real time, a comprehensive medical record of the subject can also be developed on a long term basis, for further treatment and analysis.

At least one aspect is directed to a wearable treatment device. The treatment device includes a cardiac sensing electrode, a treatment electrode, a user interface, and a sensor. The cardiac sensing electrode can be positioned outside a body of the subject and can detect cardiac information. The treatment electrode can be positioned outside the body of the subject and can apply treatment to the subject. The user interface can receive quality of life information from the subject. The sensor can be positioned outside the body of the subject and can detect subject activity and wellness information indicative of a general wellness of the subject. The treatment device also includes a controller. The controller can communicatively couple to the cardiac sensing electrode, the treatment electrode, the user interface, and the sensor. The controller receives the detected cardiac information, the quality of life information, and the detected subject activity and wellness information, and determines that treatment is to be applied to the body of the subject based upon the detected cardiac information. The controller can also adjust the treatment based on at least one of the detected subject activity and wellness information and the quality of life information. The treatment device can also include an alarm module to provide an alarm after the cardiac information is detected and before the treatment is applied to the body of the subject.

At least one other aspect is directed to a method of facilitating care of a subject. The method includes acts of sensing cardiac information of the subject, sensing subject activity and wellness information of the subject, and receiving quality of life information from the subject. The method determines that treatment is to be applied to the subject based upon the cardiac information, and adjusts the treatment based on at least one of the detected subject activity and wellness information and the quality of life information. The method also alerts at least one of the subject, a rescuer, a bystander, and a health care provider of a treatment regimen subsequent to sensing the cardiac information, and applies the treatment to the subject subsequent to alerting at least one of the subject, the rescuer, the bystander, and the health care provider of the treatment regimen.

At least one other aspect is directed to a method of facilitating care of a subject. The method includes an act of providing a wearable treatment device. The wearable treatment device includes a cardiac sensing electrode and a treatment electrode. The wearable treatment device also includes a user interface to receive quality of life information from the subject, and a sensor to detect subject activity and wellness information indicative of a general wellness of the subject. The wearable treatment device also includes a controller. The controller can couple with the cardiac sensing electrode, the treatment electrode, the user interface, and the sensor, to receive the detected cardiac information, the quality of life information, and the detected subject activity and wellness information. The controller determines that treatment is to be applied to the body of the subject based upon the detected cardiac information. The treatment can be adjusted under the direction of the controller and based on at least one of the detected subject activity and wellness information and the quality of life information. An alarm module can provide an alarm after the cardiac information is detected and before the treatment is applied to the body of the subject.

In various embodiments, the alarm module can provide a second instance of the alarm after the treatment is applied to the body of the subject. The user interface can prevent application of the treatment to the body of the subject. In one embodiment, the treatment device includes a second sensor. The second sensor can be positioned outside the body of the subject and can detect subject activity and wellness information. The controller can determine that the treatment device is properly positioned on the subject based at least in part on a position of the first sensor and a position of the second sensor.

In some embodiments, the controller can provide at least one of the cardiac information and the subject activity and wellness information to a computer server via a network. The controller can also generate a report based on the cardiac information and the subject activity and wellness information. The report may suggest a change in at least one of a treatment regimen, an exercise regimen, and a diet regimen.

In various embodiments, a wearable treatment device is provided that includes a cardiac sensing electrode, a treatment electrode, a user interface, a sensor; and a controller. The cardiac sensing electrode and the treatment electrode are positioned outside the subject. The sensor is positioned to detect the subject activity and wellness information of the subject, and the user interface receives the quality of life information. In some embodiments, the wearable treatment device substantially continuously senses at least one of cardiac information and subject activity and wellness information, and provides at least one of the cardiac information and the subject activity and wellness information to a computer server via a network. The wearable treatment device can also generate a report based on the cardiac information and the subject activity and wellness information, or suggest a change in at least one of a treatment regimen, an exercise regimen, and a diet regimen.

In some embodiments, instructions are provided to operate the wearable treatment device. The instructions include at least one instruction to position at least one of the cardiac sensing electrode and the sensor on the subject. The instructions can also include at least one instruction to position the wearable treatment device on the subject.

In another embodiment, a system including an ambulatory medical treatment device is provided. The ambulatory medical treatment device includes a memory, a treatment component configured to treat a patient, at least one processor coupled to the memory and the treatment component, a user interface component, and a system interface component. The user interface component is executed by the at least one processor and is configured to receive an update session request and to generate the update session identifier responsive to receiving the request. The system interface component is executed by the at least one processor and configured to receive an encoded request including an identifier of an update session and device update information, to decode the encoded request to generate a decoded request including the device update information and the identifier of the update session, to validate the decoded request by determining that the update session identifier matches the identifier of the update session, and to apply the device update information to the ambulatory medical treatment device.

In the system, the device update information may include information descriptive of at least one of a treatment protocol to be executed by the ambulatory medical treatment device using the treatment component and device settings to be applied to the ambulatory medical treatment device. Further, the system interface component may be configured to decode the encoded request by decrypting the encoded request. The system interface component may also be further configured to detect at least one of success and failure of the update session and rollback any device update information applied in response to failure of the update session.

The system may further include a display coupled to the at least one processor, and the user interface component may be further configured to display the update session identifier on the display and display an indication of at least one of success and failure of the update session on the display. In the system, the memory may store a device identifier that uniquely identifies the ambulatory medical treatment device, the encoded request may further include an identifier of the ambulatory medical treatment device, and the system interface component may be configured to further validate the decoded request by determining that the device identifier matches the identifier of the ambulatory medical treatment device. The memory may store a patient identifier uniquely identifying the patient assigned to the ambulatory medical treatment device, the encoded request may further include an identifier of the patient, and the system interface component may be configured to further validate the decoded request by determining that the patient identifier matches the identifier of the patient. The patient identifier and the identifier of the patient may include biometric identifiers.

The system may further include a computer system configured to receive an authorization request, verifying the authorization request, establish, in response to verifying the authorization request, a secure communication channel with the ambulatory medical treatment device, and transmit the update session request to the ambulatory medical treatment device via the secure communication channel. The computer system may be further configured to receive an authentication request including the identifier of the update session, generate the decoded request, encode the decoded request to generate the encoded request, and transmit the encoded request to the ambulatory medical treatment device via the secure communication channel.

According to another embodiment, a computer system is provided. The computer system includes a memory storing ambulatory medical treatment device update information, at least one processor coupled to the memory, and a support interface component executed by the at least one processor and configured to receive an authorization request, to verify the authorization request, to establish a secure communication channel with an ambulatory treatment device in response to the authorization request, to receive an authentication request including an identifier of an update session, to generate a request including the device update information and the identifier of the update session, to encode the request to generate an encoded request, and to transmit the encoded request to the ambulatory medical treatment device via the secure communication channel.

In the system, the support interface component may be configured to encode the request by encrypting the request. The device update information may include information descriptive of at least one of a treatment protocol to be executed by the ambulatory medical treatment device and device settings to be applied to the ambulatory medical treatment device. The memory may further store a device identifier that uniquely identifies the ambulatory medical treatment device and the request may further include the device identifier of the ambulatory medical treatment device. The memory may further store a patient identifier that uniquely identifies the patient assigned to the ambulatory medical treatment device and the request further includes the patient identifier. The patient identifier may include a biometric identifier that is unique to the patient.

According to another embodiment, a method executed using an ambulatory medical treatment device is provided. The method includes acts of receiving an update session request, generating, responsive to receiving the request, the update session identifier, receiving an encoded request including an identifier of an update session and device update information, decoding the encoded request to generate a decoded request including the identifier of the update session and the device update information, validating the decoded request by determining that the update session identifier matches the identifier of the update session, and applying the device update information to the ambulatory medical treatment device in response to validating that the update session identifier matches the identifier of the update session.

The ambulatory medical treatment device may include a display and the method may further include an act of displaying the update session identifier on the display. The encoded request may further include at least one of an identifier uniquely identifying the ambulatory medical treatment device and an identifier uniquely identifying a patient assigned to the ambulatory medical treatment device and validating the decoded request may include at least one of determining that a device identifier stored on the ambulatory medical treatment device matches the identifier of the ambulatory medical treatment device included in the encoded request, and determining that a patient identifier stored on the ambulatory treatment device matches the identifier of the patient-included in the encoded request.

In the method, the act of determining that the patient identifier stored on the ambulatory medical treatment device matches the identifier of the patient included in the encoded request may include comparing biometric identifiers. The method may further include an act of receiving, by a computer system, a authorization request, verifying the authorization request, establishing, in response to verifying the authorization request, a secure communication channel with the ambulatory medical treatment device, transmitting the update session request to the ambulatory medical treatment device via the secure communication channel, receiving an authentication request including the identifier of the update session, generating the decoded request, encoding the decoded request to generate the encoded request, and transmitting the encoded request to the ambulatory medical treatment device via the secure communication channel. In the method, support personnel may instruct a patient to enter the request to generate an update session identifier and the support personnel may enter the request to initiate the update session.

Other aspects, embodiments, and advantages of these exemplary aspects and embodiments are discussed in detail below. Both the foregoing information and the following detailed description are illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain the described and claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
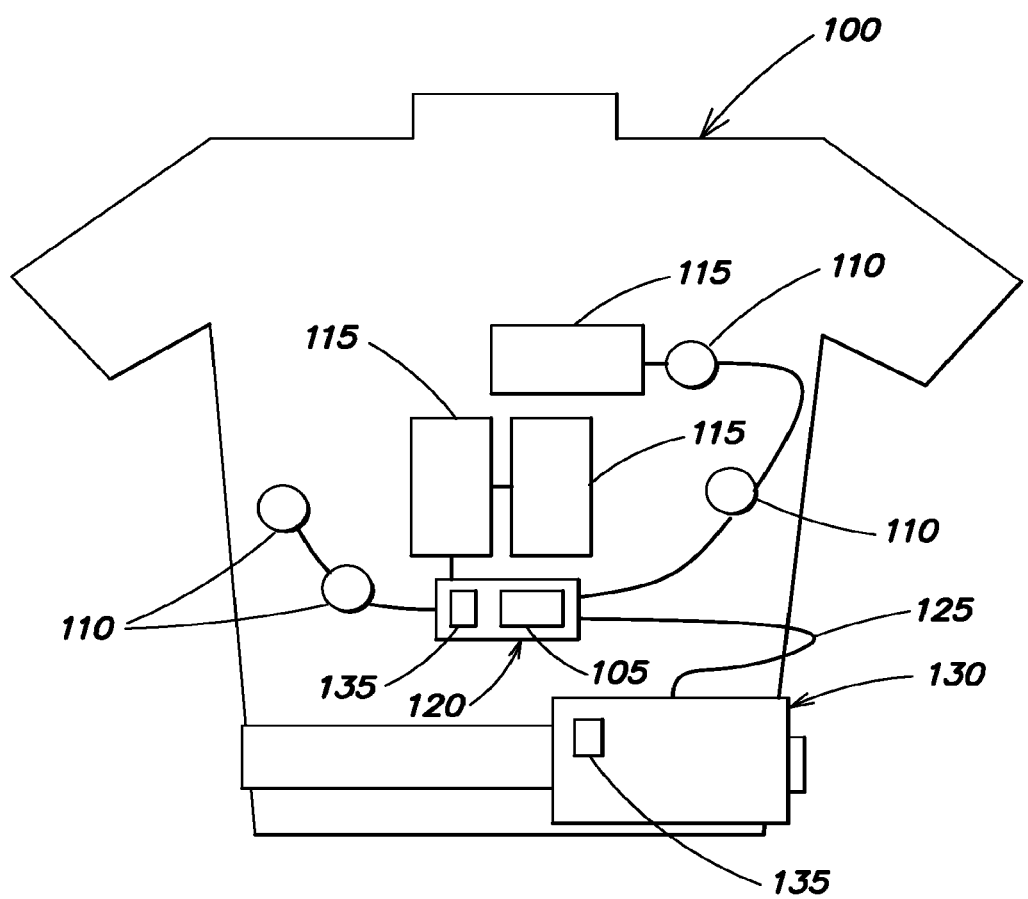
FIG. 1 depicts a diagrammatic representation of treatment device positioning on a subject in accordance with an embodiment.

The systems and methods described herein are not limited in their application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including" "comprising" "having" "containing" "involving" and variations thereof herein, is meant to encompass the items listed thereafter, equivalents thereof, and additional items, as well as alternate embodiments consisting of the items listed thereafter exclusively.

Various aspects and embodiments are directed to a wearable treatment device that senses information about a subject's condition. This information includes cardiac information, subject activity and wellness information, and subject quality of life information. This information can be aggregated into reports on the subject's condition that can be used to provide or adjust treatment regimens. An alarm module can indicate that treatment has been, is being, or will be applied.

FIG. 1 illustrates wearable treatment device 100 configured for a subject to wear as a garment. The subject includes a person receiving health care, such as a subject who may or may not be under supervision of a doctor or health care provider. The subject may be in or out of a hospital setting, and the subject can engage in day to day life activities, at home, work, leisure, and play while wearing treatment device 100. Treatment device 100 includes monitoring, treatment and data transmission and processing capability, and can be worn as a vest, belt, shirt, or series of straps, garment, or undergarment for example. Treatment device 100 may include at least one power supply such as a battery, or other power supplies, including AC power supplies and uninterruptable power supplies. Treatment device 100 can monitor and treat cardiac ailments such as heart failure, as well as other medical conditions such as arrhythmias, pulmonary ailments, other heart irregularities, sleep disorders, and circulatory system deficiencies such as blockages.

In one embodiment, treatment device 100 includes dedicated control logic devices that collectively constitute a control system, such as at least one controller 105. Controller 105 can include programmable logic devices and arrays, application specific integrated circuits, hardware and software combinations, general purpose processors and dedicated controllers, for example. Further, treatment device 100 may include graphical user interfaces or other interfaces to provide output information and receive input information from a user. Controller 105 can be contained entirely within treatment device 100, or at least partially located external to treatment device 100, such as at a remote computer server in a doctor's office, data center, or other location. In one embodiment, controller 100 includes at least one processor as described in commonly owned U.S. patent application Ser. No. 12/833,096, entitled "System and Method for Conserving Power in a Medical Device," filed on Jul. 9, 2010, which is incorporated by reference herein in its entirety. The referenced application generally discloses a processing architecture configured to conserve energy.

Treatment device 100 can also include a plurality of sensors 110, 135. The plurality of sensors 110, 135 may include subject medical condition sensors 110, such as cardiac sensing electrodes, and subject activity sensors 135, such as motion sensors or accelerometers. While four external medical condition sensors 110 are illustrated in FIG. 1, treatment device 100 can include more or less than four external medical condition sensors 110, and in some embodiments, sensors 110 include at least one internal sensor or external dry electrode. Sensors 110 may include at least one cardiac sensing electrode to detect a subject's cardiac information related to the subject's heartbeat or electrical activity of the subject's heart. Sensors 110 are configured for placement proximate to the subject, for example, about the subjects torso, chest, back, limbs, or neck, where they can sense information about the subject's bodily functions. In one embodiment, sensors 110 include a fingertip pulse oximeter that can generate a photoplethysmograph to measure blood flow, blood oxygen saturation, respiration, or hypovolemia. In other embodiments, sensors 110 can include sensors that monitor or measure wellness information indicative of a general wellness of the subject, such as pulse, breathing, temperature, blood pressure, or fatigue information, for example.

In one embodiment, the plurality of sensors 110, 135 includes subject activity sensors 135. In one embodiment, subject activity sensors 135 can include at least one accelerometer to detect subject movement, lack thereof, or positional orientation. Sensors 110, 135 that include subject activity sensors generally detect tangible medical or physical condition or information indicative of a subject's overall health, as well as statistically significant changes in measurements or conditions with time that may indicate changes in the subject's health, such as a worsening heart failure condition.

Treatment device 100 may also include at least one treatment electrode 115. In one embodiment, treatment electrode 115 is configured to deliver shocks or electric current to the subject, such as a defibrillation shock applied to resuscitate a subject during cardiac arrest or another cardiac event. Treatment electrodes 115 may be housed in therapy pads that also include receptacles to house conductive fluid such as conductive gel. For example, treatment electrodes 115 may include dry treatment electrodes. In this example, prior to treatment, controller 105 can direct the receptacle to burst, releasing conductive fluid that contacts a surface of treatment electrode 115 as well as the subject's skin, enhancing the electrical connection between the subject and treatment electrode 115. The receptacles can be replaced after use.

In one embodiment, treatment electrodes 115 are formed from plates of metal or other conductive material having a conductive surface and configured for contact with the subject. The therapy electrodes may have generally circular, oval, rectangular, square, or other geometric forms with a generally continuous surface. In some embodiments, treatment electrodes 115 are formed from conductive wire or thread sewn into treatment device 100 in stitched, woven, or intertwined patterns, including a mesh pattern. In one embodiment, treatment device 100 includes at least one node 120 to connect or interface with sensors 110 and treatment electrodes 115. Node 120 may be located on a belt of treatment device 100 and can be part of or associated with controller 105 to facilitate communication between controller 105, sensors 110, 135 and treatment electrodes 115. In one embodiment, node 120 is a device to physically couple cables 125 that connect controller 105, sensors 110, 135 treatment electrodes 115, and other treatment device 100 components, such as at least one monitor 130. FIG. 1 depicts three treatment electrodes 115, with one treatment electrode positioned proximate to the subject's chest, and two treatment electrodes 115 positioned proximate to the subject's back. This configuration can be used to provide shocks to the subject's heart during defibrillation treatment. Other configurations and positions of treatment electrodes 115 are possible for defibrillation and other treatments.

In one embodiment, treatment device 100 includes at least one subject activity sensor 135. For example, subject activity sensor 135 may include at least one accelerometer that can indicate accelerating and decelerating movements. For example, a subject wearing treatment device 100 can participate in normal activities, such as standing, walking, sitting, running, and generally moving about as part of day-to-day life when partaking in physical, labor, and leisure activities. Because of the nature of human movements, generally comprising short distance and short duration, accelerometers provide useful information about subject movement and activity. Controller 105 can use this information to determine if treatment is necessary or should be adjusted, if quality of life recommendations should be made to the subject (e.g., a suggestion to change dietary or activity habits) or if a doctor should be consulted. In some embodiments, activity sensors 135 include single axis accelerometers as well as multi-axis sensors.

In one embodiment, the plurality of sensors 110, 135 include at least one cardiac sensing electrode 110, a subject activity sensor 135, such as an accelerometer, or other sensor configured to provide information to controller 105 relating to the subjects cardiac information (e.g., ECG), or activity wellness (e.g., motion or position). For example, sensor 135 can sense and provide information about the subject's body state—e.g., vertical, horizontal, lying down on left side, lying down on right side, moving in a recitative pattern, vibrating due to environmental causes such as during a car ride, convulsing due to health causes such as a cardiac event or seizure, accelerating, decelerating, falling, and treatment device 100 component acceleration or mechanical shock, (e.g., sensor 135 disconnects from the subject and falls or impacts the ground or a hard surface due to gravitational or other forces).

In one embodiment, treatment device 100 includes two activity sensors 135, such as accelerometers. For example, a first accelerometer can be located on node 120 and a second accelerometer can be located on monitor 130. In one embodiment, the first accelerometer is positioned on the subject's upper body, and the second accelerometer 135 is positioned proximate to the subject's waist. Accelerometers or other activity sensors 135 may also be positioned on the subject's limbs. Activity sensors 135, including accelerometers, may include at least one position, force, or motion detector. In one embodiment, controller 105 uses information detected by multiple activity sensors 135, such as accelerometers to determine and predict subject activity, and to calibrate or verify the accuracy of sensors 110 and/or sensors 135. For example, one or more of sensors 110 may be tasked with determining the subject's heart beat, and may shift due to movement or be improperly positioned so that an inaccurate reduced heartbeat is sensed. In this example, activity sensors 135 may indicate that the subject is exercising and where an elevated heartbeat would be expected, while sensor 110 detects a reduced heart beat or no heart beat because it is improperly positioned on the subject. Controller 105 can identify this discrepancy and notify the subject, for example by a display on monitor 130, that one of sensors 110 should be repositioned. By processing sensed information and information received from the user, controller 105 may also determine that treatment device 100 components have been tampered with or damaged, and monitor 130 can display a notification of any such tampering or damage. In one embodiment, controller 105 is located together with monitor 130.

In one embodiment, controller 105 evaluates activity sensor 135 information to determine the position of the subject and any corresponding applied forces. For example, activity sensor 135 can measure x, y, and z axis orientations of the subject. Controller 105 can use this information in a confidence based arrhythmia detection algorithm to accelerate or delay the timing of treatment based on past and present body motion or position history. Multiple activity sensors 135 permit separate evaluation of different subject movements and controller 105 evaluates subject movements to determine subject activity, create a real time and comprehensive subject medical record, and to recommend, apply, or adjust treatment regimens. The treatment applied can depend upon the diagnostic requirement of the subject's doctor and the condition of the subject (e.g., heart failure or congestive heart failure) that the doctor or the subject wishes to monitor.

In one embodiment, activity sensors 135 include at least one accelerometer to sense high sensitivity subject activity and wellness information, such as breathing or other generally subtle forms of motion such as body position (e.g., standing or prone). Sensors 110, 135 can detect and monitor physical activity and activity trends, body positions, and sleep conditions, such as sleep apnea. For example, sleep apnea may be deduced based on pulse oximetry and respiration measurements. Sensors 135 can also include at least one accelerometer to measure low sensitivity data such as mechanical shock.

In some embodiments, activity sensors 135 include at least one multi-axis accelerometer, or two three-axis accelerometers with one of the accelerometers mounted on a vest portion of treatment device 100 and another of the accelerometers mounted elsewhere on treatment device 100, such as a strap about the waist, or on monitor 130, which can include a visual display where the orientation of the visual display is controlled by the output of accelerometer.

In one embodiment, treatment device 100 includes at least one monitor 130, which can include at least one touch screen, buttons, or other user interface such as a keyboard. The user interface may have multilingual audio and visual displays. Monitor 130 can also be remote from treatment device 100. Monitor 130 can display information to indicate that treatment device 100 is or is not properly configured about the subject. For example, monitor 130 can indicate that sensors 110, 135 are properly positioned and operational. Monitor 130 can attach to a belt or other portion of treatment device 100. In one embodiment, monitor 130 can be exposed, external to the subject's clothing, with at least some other treatment device components (e.g., sensors 110, 135) concealed beneath the subject's clothing. In one embodiment, treatment device 100 includes two monitors 130, with a first monitor housed on treatment device 100, and a second monitor remote to treatment device 100. The second monitor can communicate with controller 105. In one embodiment, the second monitor displays additional information that the first monitor does not display. For example, the second monitor can be part of a base station or a battery charger that includes a processor and memory. The second monitor can also be a personal computer monitor, (e.g., laptop, desktop, tablet, or mobile telephone monitor) configured to display the subject's historical medical record and other long term non-critical information, and the first monitor can be a dedicated application specific monitor that is housed on a belt of treatment device 100 configured to input and output core data related to the subject's present cardiac condition, general wellness, quality of life, and treatment regimen.

In one embodiment, monitor 130 displays medication reminders to prompt the subject to take medication. For example, monitor 130 can display visual information (that can be supplemented with audio information) telling the subject what medication to take, and when. In one embodiment, monitor 130 shows the subject what the medication (e.g., a pill) looks like (for example, by color, shape, markings, etc.), and issues a verbal prompt to remind the subject to take a certain medication and a certain time. After taking the medication, the subject can inform treatment device of this fact via a user interface of monitor 130.

Monitor 130 may also include an alarm module. The alarm module can be audio, visual, tactile, or haptic, and can alert the subject as well as bystanders that treatment device 100 has applied, is applying, or will apply electric current or other treatment to the subject. The alarm module can also provide indicators of the subject's condition, such as heart or respiration rates, volume, or timing, or the subject's pulse, as well as heart failure indicators and coronary sounds.

In one embodiment, the alarm module provides an alarm after sensor 110 detects cardiac information about the subject, and before treatment device 100 applies treatment to the subject. The alarm module can also provide a further alarm after treatment has been applied to the subject. For example, the alarm module can alert first responders that at least one defibrillation shock has already been applied by treatment device 100. The alarm module can also alert bystanders or rescuers that it is safe to contact the subject after treatment has been applied, or that another round of treatment (e.g., another shock) is forthcoming. In one embodiment, the alarm module indicates that treatment will be applied. When the subject does nothing to abort the forthcoming treatment (such as depressing an abort switch or entering instructions via the user interface) controller 105 can instruct treatment device 100 to administer an electric shock to the subject via one of treatment electrodes 115.

In FIG. 1, a first activity sensor 135 such as an accelerometer is located in front of the subject, for example attached to monitor 130, and a second activity sensor 135, such as an accelerometer is located in back of the subject, for example attached to a belt of treatment device 100. Other configurations of accelerometers are possible, in front, in back, and on the sides of the subject, and attached to different belts, straps, or other components of treatment device 100. Wire 125 allows communication and data transfer between activity sensor 135, medical condition sensors 110, and controller 105 via node 120.

Figure 2:
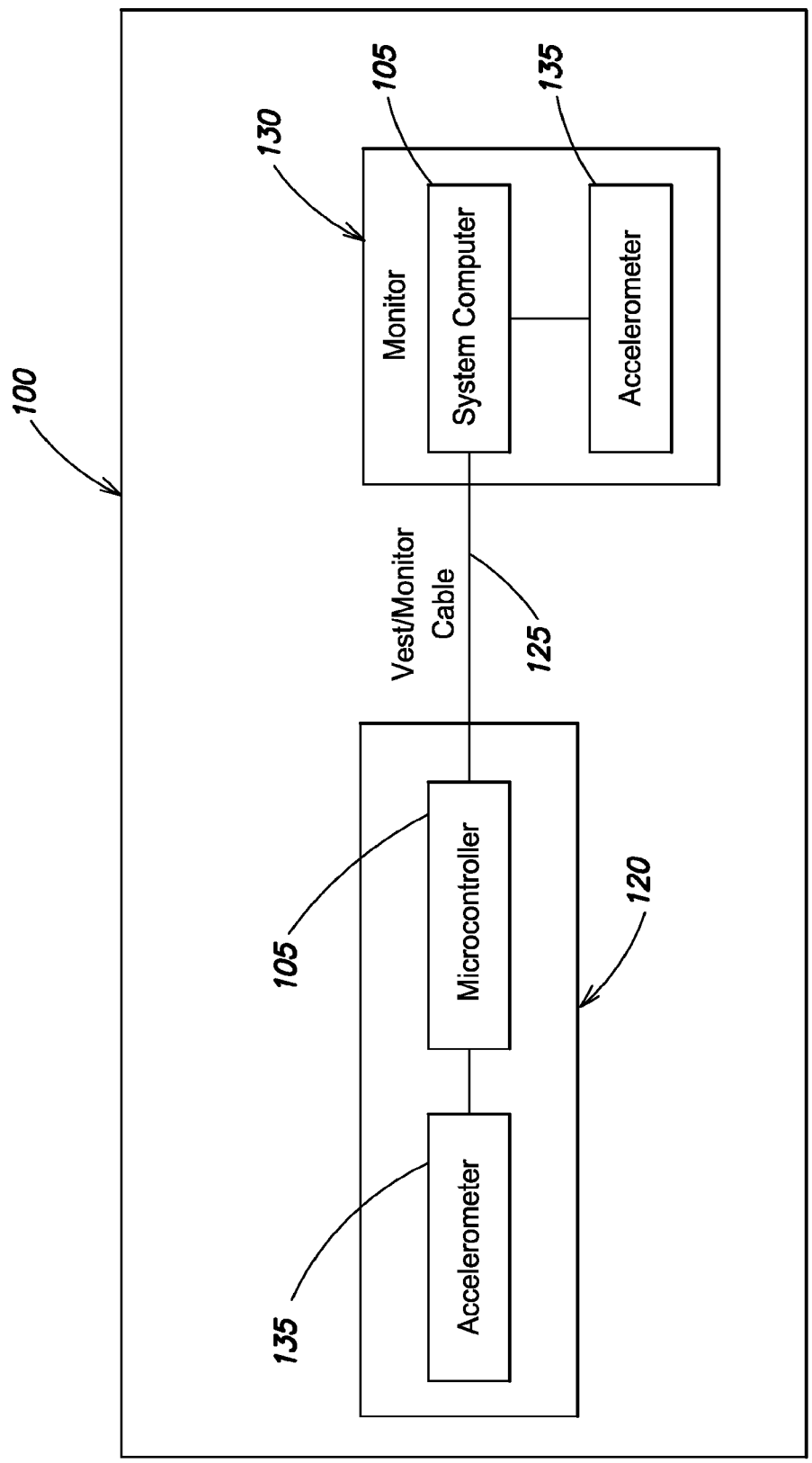
FIG. 2 depicts a block diagram of a treatment device in accordance with an embodiment.

FIG. 2 depicts a block diagram of treatment device 100. As illustrated in FIG. 2, controller 105 includes a microcontroller and a system computer, with the microcontroller associated with node 120 and the system computer associated with monitor 130, and with wire 125 connecting the microcontroller with the system computer. Different configurations are possible. For example, more than one logic device can collectively constitute controller 105, and controller 105 may be part of treatment device 100. In one embodiment, at least some logic devices of controller 105, such as the system computer, are located external to treatment device 100. For example, both monitor 130 and the system computer can be separate from treatment device 100. Such external components may communicate with the microcontroller or other elements of controller 105 that are part of or housed on treatment device 100 via wire 125 or other connections, both wired and wireless. In one embodiment, the microcontroller process real time information related to the subject's cardiac information, quality of life, general wellness, and treatment regimen; and the system computer processes information related to the subject's long term medical history. For example, controller 105 can provide information to a remote computer via a wireless transmission to generate a comprehensive real time medical history of the subject when, for example, the subject wears treatment device 100 for any period of time. This medical history information may be stored in memory that is part of treatment device 100, or remotely, for example in a hard drive of a computer in a doctor's office. The system computer and the microcontroller can exchange information and instructions regarding treatment application and adjustment. In one embodiment, controller 105 communicates a message to a physician, responder, bystander or the subject to indicate that treatment is imminent, being provided, or has already been provided.

In one embodiment, controller 105 communicates with a central server that is external to treatment device 100. For example, sensed indicators of heart failure can be wired or wirelessly downloaded to a central server for processing, and presented to a doctor for review and analysis. This information can be tailored to a doctor's needs, for example to generate alerts and notifications. With respect to data gathering, reference is made to U.S. Pat. No. 6,681,003, entitled "Data Collection and System Management for Patient-Worn Medical Devices," filed on Jul. 16, 2002, which is assigned to the assignee of the present application and incorporated herein by reference in its entirety. The referenced application generally discloses remote transmission and collection of data received from patient-worn medical devices.

In one embodiment, a first activity sensor 135, such as an accelerometer, is attached to node 120 and a second activity sensor 135, such as another accelerometer, is attached to monitor 130. Sensed information from both of these sensors 135 can be transferred to controller 105, which can be physically attached to treatment device 100, or remote from treatment device 100. In one embodiment, treatment device 100 includes two accelerometers to determine parameters such as subject body position, body movement, and body acceleration, and to perform self-diagnostics. Monitor 130 can contain either a high-G or a low-G accelerometer, or both. In one embodiment, a high-G low-sensitivity accelerometer can detect subject and equipment physical shock to determine if treatment device 100 is damaged.

Activity sensors 135 can detect movement and orientation of the subject. In one embodiment, controller 105 processes information from two activity sensors 135, such as accelerometers 135 to identify subject activity. Processing of accelerometer data can be performed by the microcontroller or the system computer. Accelerometers can indicate change in the subject's velocity. For example, the subject can have an activity level when conscious that includes changes in both velocity and direction. By contrast, an unconscious subject may have little or no change in body motion. Other activity sensors 135 (e.g., gyroscope, magnetometer, hall-effect devices, pedometers, global positioning systems, and other force motion or position sensors) can indicate motion or lack of motion. Outputs from sensors 135 may be integrated, compared or differentiated by controller 105 to predict subject activity, and reduce interference or error signals.

Figure 3:
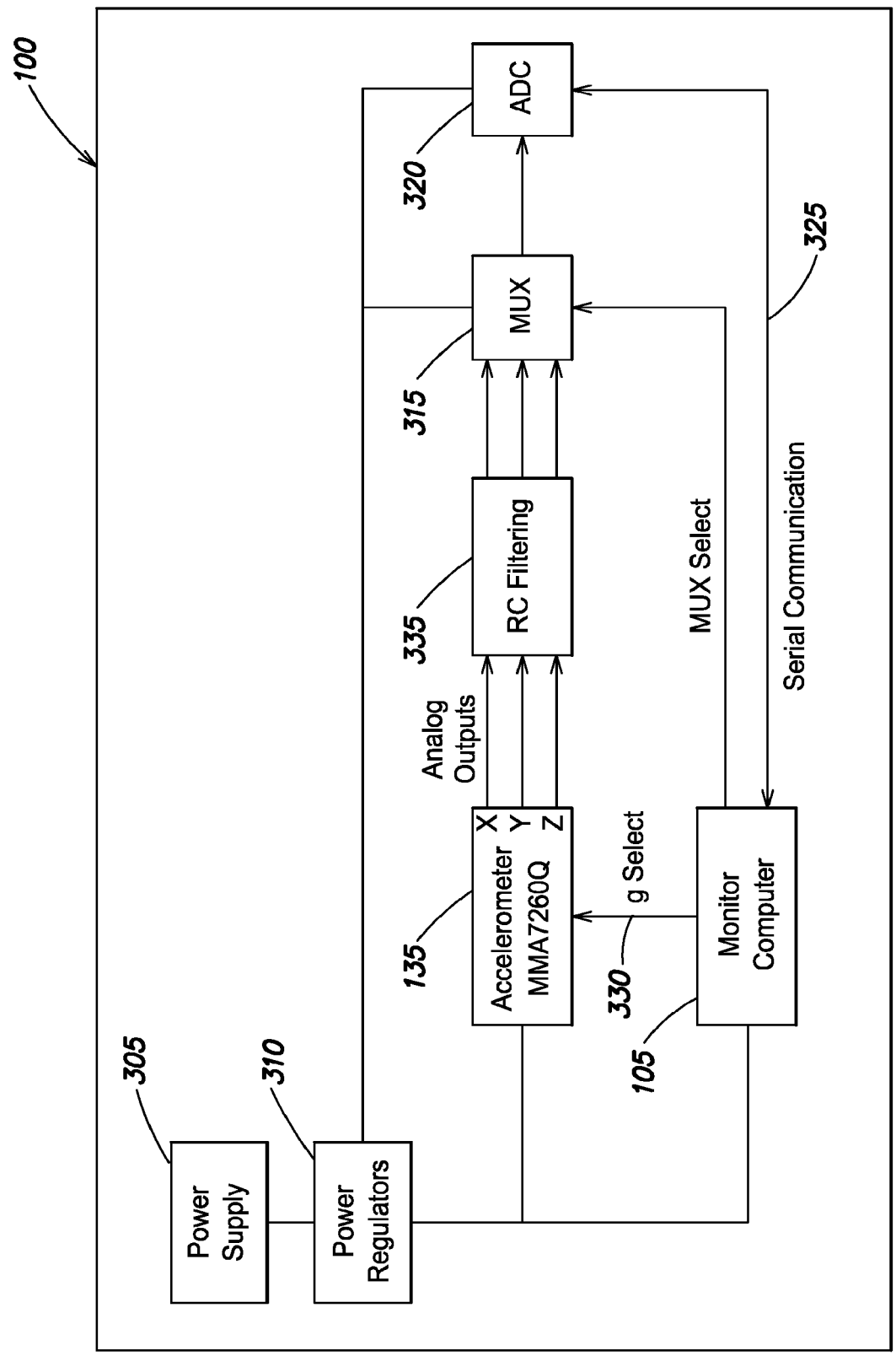
FIG. 3 depicts a block diagram of a treatment device in accordance with an embodiment.

FIG. 3 depicts a block diagram of a treatment device 100. In one embodiment, AC or DC power supply 305 (e.g., a power cord to AC main lines, or a battery) can power treatment device 100 components, such as controller 105, monitor 130, and sensors 110, 135. At least one power regulator 310 can control the power from power supply 305.

In one embodiment, controller 105 controls various system parameters such as activity sensor sensitivity, multiplexer (MUX) 315 channel select, the analog to digital converter (ADC) 320, and serial communication with controller 105 via serial communication bus 325 to acquire data from activity sensors 135 and to display this information at monitor 130. MUX 315 and ADC 320 can be internal to controller 105, or can be separate components. In one embodiment, activity sensors 135 include a Freescale Semiconductor MMA7260Q three axis low-g micromachined accelerometer. The g-select control line 330 coupled to controller 105 and the accelerometer allows the sensitivity to be varied from, for example, 1.5 g to 6 g. A high-G low sensitivity accelerometer can also be used to allow subject/equipment shock to be detected. Resistor-capacitor (RC) filter 335 can connect to outputs of the accelerometer to minimize clock noise from the accelerometer internal switched capacitor filter circuit. Controller 105 can control select lines of multiplexor 315 and may allow each axis output of the accelerometer to be switched to the Analog to Digital Converter (ADC) 320 input. Controller 105 can also control ADC 320 via a serial interface. In one embodiment, sensors 110, 135, controller 105, and monitor 130 sense, process, and display other information such as sensed cardiac information, sensed general wellness information, and subject inputted self assessment entries including quality of life information.

Figure 4:
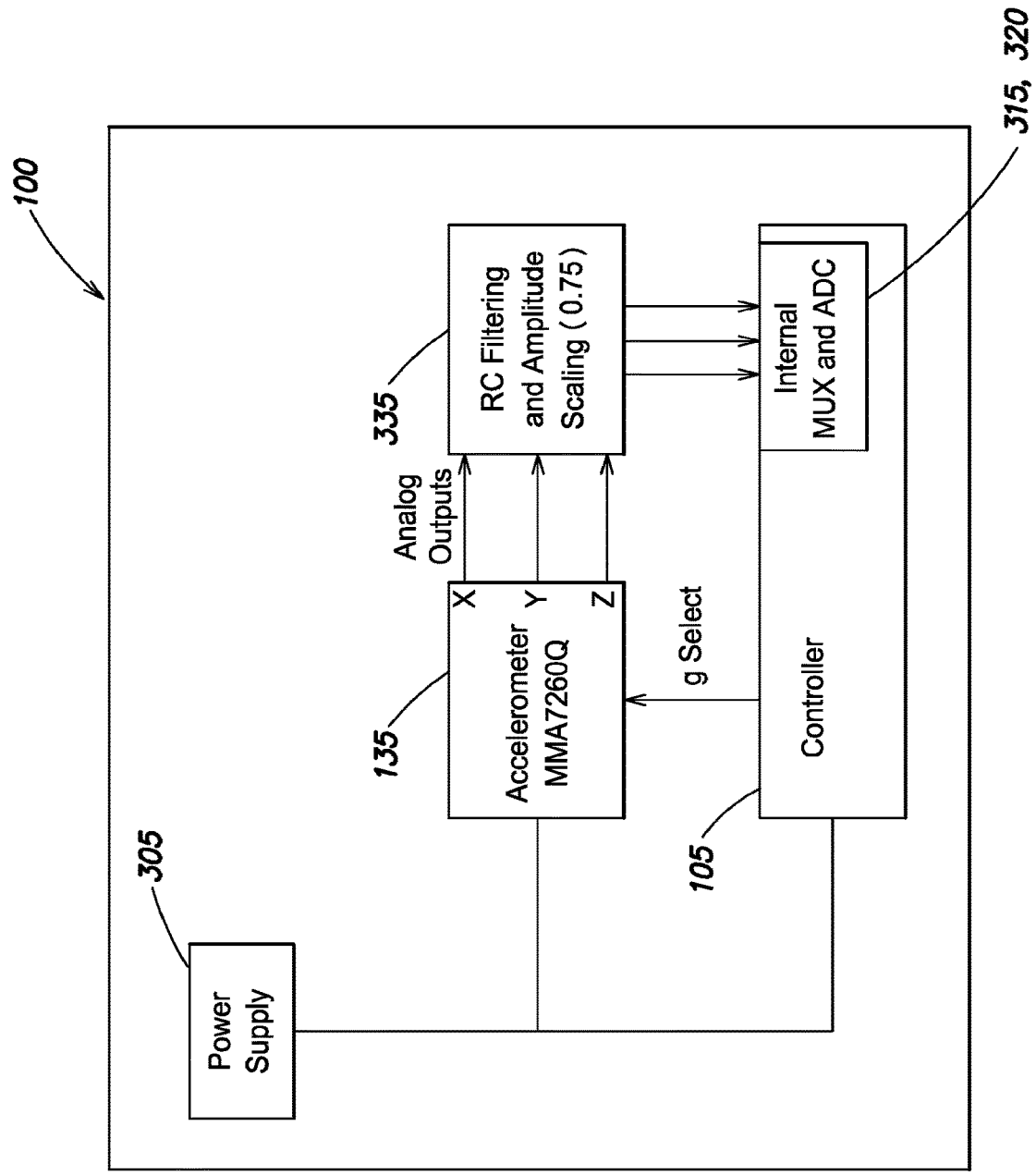
FIG. 4 depicts a block diagram of a treatment device in accordance with an embodiment.

FIG. 4 depicts an alternative block diagram of a treatment device 100 where controller 105 acquires information from activity sensor 135, such as an accelerometer. Power supply 305 can be used to power the components of treatment device 100. Activity sensor 135 can include a Freescale Semiconductor MMA7260Q three axis low-g micromachined accelerometer. Controller 105 controls the g-select lines that again can allow the sensitivity to be varied from, for example, 1.5 g to 6 g. RC filter 335 as well as amplitude scaling can be applied to each of the accelerometer outputs. In one embodiment, MUX 315 and ADC 320 are internal to controller 105 the analog outputs of the accelerometer are interfaced digitally directly to the controller 105.

In one embodiment, controller 105 detects an arrhythmia by assigning various confidence coefficients or weighting values to the various sensors 110, 135) that communicate with controller 105. In one embodiment, this is done prior to controller 105 determining a confidence level that detected motion indicates true motion, and not a false positive motion indication due, for example, to an incorrectly placed or dropped activity sensor 135. For example, controller 105 can separately analyze two independent ECG data streams from sensors 110 to extract heart rate, morphology, frequency information, general wellness, and other information. Controller 105 can perform additional analysis, independently on each channel, to analyze the signal for noise contamination that may result from subject motion or biological signals such as muscle noise. Secondary inputs to the basic detection algorithm can include a subject response button or override switch, where for example the subject indicates that they are in motion, and inputs from activity sensors 135. In one embodiment, controller 105 determines that the lack of response from the subject, for example, by not pressing a subject response button (e.g., an abort switch) that can be part of treatment device 100, means that the subject is unconscious.

In one embodiment, a weighting value is assigned to each sensor 110, 135 and the response button to make the decision that a treatable arrhythmia condition exists. In addition, the weighting values can be used to manipulate or adjust the timing and nature of therapy delivered by therapy electrodes 115.

During use by a subject, there may be instances where a first ECG channel contains noise and a second ECG channel is clean. For example two pairs of sensors 110 can independently obtain ECG signals, with one pair being contaminated with artifacts and the other being clean. The two ECG signals can be obtained simultaneously or sequentially, and can be transmitted to controller 105 via the same or different communication channels (e.g., wire 125). In one embodiment, controller 105 places more weight on the clean ECG channel. For example, to enhance a confidence level of the sensed information, a weighting can be assigned that would delay delivery of treatment by treatment electrodes 115 while sensors 135 and controller 105 determine if there is subject motion.

Figure 5:
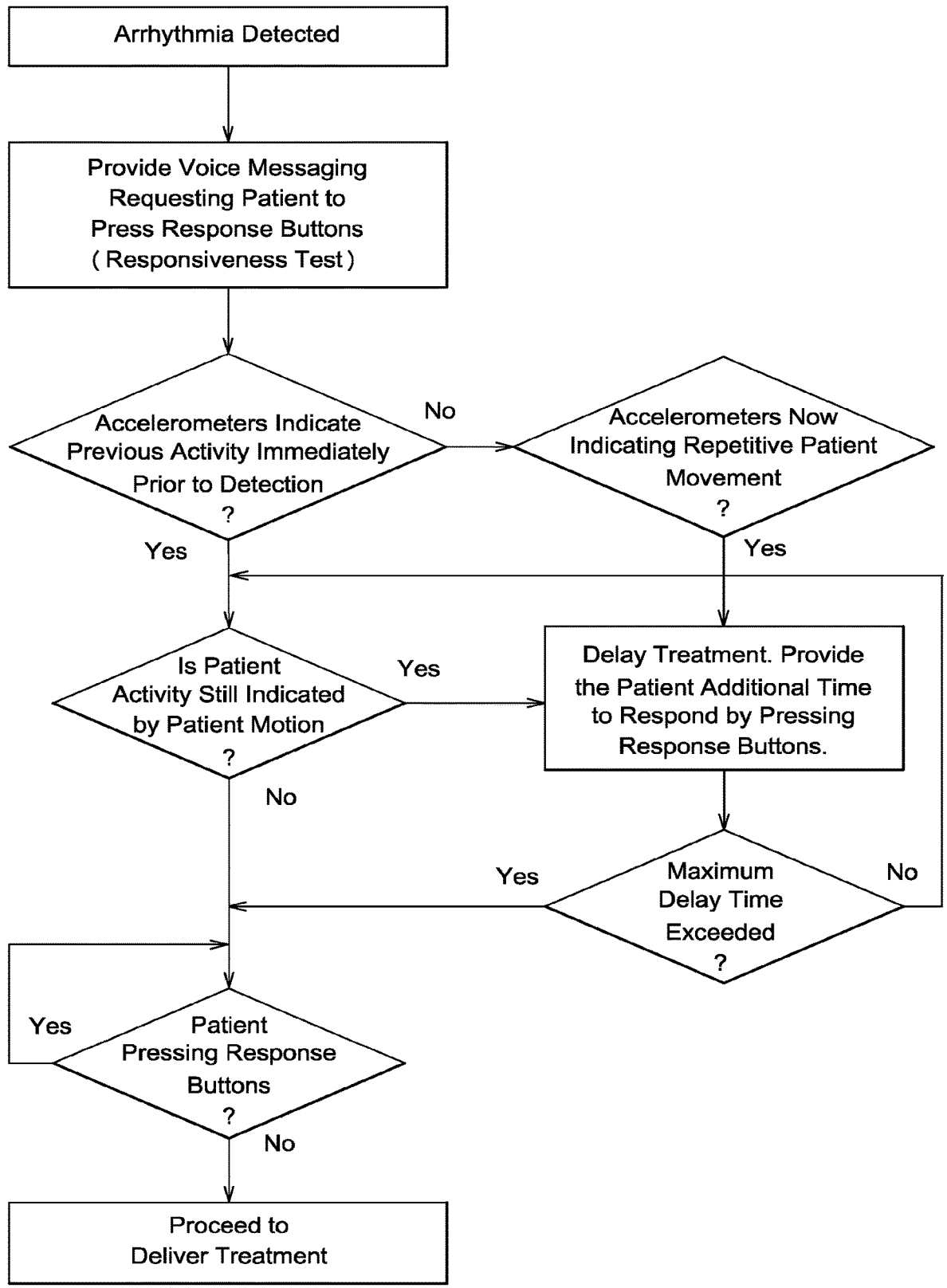
FIG. 5 depicts a flow chart for a method of monitoring and treating a subject in accordance with an embodiment.

The flow diagram in FIG. 5 shows that if subject motion is detected prior to the detection of a treatable arrhythmia, the timing of treatment delivery can be modified based on activity sensor 135 inputs when the arrhythmia is detected. If the subject becomes motionless coinciding with the arrhythmia detection, there is an increased confidence that the arrhythmia diagnosis is accurate and the delivery of treatment can occur sooner. If motion continues after the arrhythmia detection, the confidence of a valid detection can be decreased because lethal arrhythmias generally result in a lack of consciousness and lack of motion. In this case, the delivery of treatment can be delayed to allow time for audio voice messages to prompt the subject to respond by pressing the response button. The response button provides a responsiveness test input to the algorithm. In some embodiments, it may be desirable to never deliver a shock to a conscious subject. This method can reduce the possibility of false treatment based on invalid rhythm diagnosis due to corrupt ECG inputs caused by excessive subject movement or other environmental factors.

FIG. 5 illustrates arrhythmia detection with increased confidence by serially feeding through a subsequent confidence algorithm using input from activity sensor 135, such as a motion detector or accelerometer. Other motion detecting devices or confidence algorithms can use various motion detection criteria as desired by physicians and based upon the treatable condition or subject. The motion data can also be stored, tracked and evaluated, for example to evaluate a subject's historical motion or activity levels to detect conditions such as congestive heart failure. Such diseases can be found in subjects wearing treatment device 100.

In one embodiment, treatment device 100 includes sensors 110 to monitor the subject's cardiac information. For example sensors 110 can include cardiac sensing electrodes that are positioned external to the subject to detect the subject's cardiac information. Controller 105 processes the sensed cardiac information to detect life-threatening arrhythmias, and can instruct treatment electrodes 115 to deliver treatment, such as a cardioverting or defibrillating shock. Treatment device 100 can also include a user interface to receive quality of life information. For example, the subject can enter information about the subject's lifestyle, eating and exercise habits, and how the subject currently feels. Additional sensors 110, 135 can detect subject activity or other wellness information, such as respiration or pulse rates, or temperature. In one embodiment, this subject activity and wellness information is discrete information that can be measured or sensed by sensors 110, 135, as opposed to quality of life information that may be of a more general nature such as what the subject ate or how the subject feels, or more subjective information provided by the subject or the subject's physician.

In one embodiment, treatment device 100 includes at least one treatment electrode 115 configured for external positioning proximate to the subject. Controller 105 communicates with sensors 110, 135 including sensors configured to sense cardiac information (e.g., cardiac sensing electrodes) and sensors configured to detect subject activity and wellness information, (e.g., accelerometers). Controller 105 can also communicate with the user interface of monitor 130. Controller 105 receives detected cardiac information, (ECG signals), detected subject activity and wellness information, and inputted quality of life information to determine if treatment is to be applied to the subject. Controller 105 can also adjust a treatment regimen, for example by advancing or delaying its application by treatment electrodes 115. For example, controller 105 can decide to apply treatment (e.g., an electric shock from therapy electrodes 115) based on sensor 110's detected cardiac information) and can adjust the treatment regimen based on sensor 110's detected subject activity and wellness information or based on the quality of life information provided by or on behalf of the subject via a user interface. In one embodiment, controller 105 adjusts therapy based on the subject's level of activity over a period of time, where information from sensors 135 is used to determine the subject's level of activity.

In one embodiment, controller 105 controls the nature and application of a treatment regimen based on information from any of sensors 110, 135 (including, for example, cardiac sensing electrodes, other sensing electrodes, accelerometers), treatment electrodes 115, the user interface of monitor 130, and other inputs of the subject's cardiac information, subject activity and wellness information, and quality of life information. Based on this information, controller 105 can determine a treatment regimen (e.g., what type of treatment) and determine that the treatment has, is, or will be applied. Based on this information, controller 105 can also adjust the treatment regimen or the application of the treatment. Controller 105 can also control an alarm module to alert the subject or others of past, present, or pending treatment.

In one embodiment, medical condition sensors 110 and controller 105 can detect and identify heart failure indicators such as heart or respiratory rates. The subject or a service provider can view a chart or graph based on the sensed information that tracks heart failure indicators over time. The display can be on a monitor that is remote from treatment device 100 via wired or wireless communication over a network, or local to treatment device 100 as part of monitor 130. Controller 105 can generate reports that summarize trends or indicators for one or more subjects. Heart failure indicators above or below a certain threshold value can trigger an alert notification to the subject via the alarm module or to a remote doctor. The heart failure information sensed by medical condition sensors 110 can be provided to the subject or a doctor in the form of a report, either on demand or periodically as part of a routine notification schedule. The report can be sent by text message, page, automated phone call or email, and can flag trends in the subject's condition, noting changes, trends, and exceptions as they occur.

Subjects wearing treatment device 100 may suffer from heart failure and develop pulmonary edema, which involves the buildup of extravascular fluid in the lungs, (e.g., congestion). Fluid can pool in blood vessels in the lungs and become a barrier to normal oxygen exchange. In one embodiment, medical condition sensors 110 monitor impedance of the subject's thoracic cavity and controller 105 processes this sensed impedance information to detect the presence or absence of pulmonary edema, which may be an indicator of heart failure. A reduction in sensed thoracic impedance indicates an increase in thoracic fluid, and fluid depletion in the thorax indicates an increase in thoracic impedance.

In one embodiment, controller 105 and sensors 110 or treatment electrodes 115 sense and measure transthoracic impedance. This data can be collected because the subject can wear treatment device 100 substantially continuously for extended periods of time. Controller 105 can average transthoracic impedance measurements over time to identify extravascular fluid buildup. By comparing the averaged measured values with thresholds, treatment device 100 can alert the subject or a doctor of changes in the subject's condition so that treatment or medical advice can be provided.

In one embodiment, treatment device 100 measures and records respiration data by monitoring transthoracic impedance changes. For example, impedance increases as air fills the lungs, and decreases when air is exhausted from the lungs during exhaling. By monitoring these and other changes with medical sensors 110 (e.g., cardiac sensing electrodes, pulse oximeters) and activity sensors 135 (e.g., accelerometers, strain gauges, pedometers, nasal clips, expandable belts, monitoring of elastic movement of treatment device 100) controller 105 can determine the subject's respiration rate, stride, pulse, and other information. Information sensed by sensors 110, 135 can be transmitted over a network (e.g., the Internet) to a doctor on demand or as part of a periodic report. The doctor can evaluate this information to make a diagnosis.

Treatment device 100 can sense and monitor a variety of conditions and trends, such as atrial fibrillation, nocturnal heart rate, respiration rate, pulmonary sounds, heart sounds, activity trends, body position trends, heart rate variability, heart rate turbulence, and bradycardia events. For example, controller 105 can processes information detected from sensors 110, 135 (e.g., ECG signals, accelerometer information, or sound information) to detect any of these conditions. In one embodiment, medical condition sensors 110 include an ECG sensing electrode system that, together with activity sensors 135 and controller 105, detect and record metrics associated with the minimum heart rate value that typically occurs during sleep, as well as diurnal heart rate. In one embodiment, sensors 110 include an auscultation sensor that records chest and lung sound recordings to identify fluid content in the lungs. In addition, sensors 110 can detect wheezing and coughing that can indicate fluid buildup and a worsening condition. In one embodiment, activity sensors 135 can detect movement that occurs during coughing to verify an indication of a cough detected by an audio sensor. Controller 105 may also analyze sensed heart audio signals to identify changes in cardiac performance.

In one embodiment, treatment device 100 detects activity or body position trends, and analyzes this information to determine the subject's condition. Controller 100 may make this analysis, or may communicate the sensed information to a computer server, where the information is analyzed remotely. For example, the physical activity of a subject with heart failure may decrease as the heart failure condition worsens. General subject activity and movement can indicate whether the heart failure conditions are getting better or worsening, and can indicate whether treatment is working. For example, information from activity sensors 135 may be used to generate activity trends of the subject's activity level (e.g., increasing with time, decreasing with time, remaining substantially constant). This information can be generated over long periods of time when the subject is wearing treatment device 100. In one embodiment, activity sensors 135 sense subject activity, including body movement and positioning throughout the day and during sleep. Sleep positioning information may include the angle of the subject body during sleep, as sleeping in an inclined position (e.g., on a reclining chair) can indicate worsening heart failure. For example, an increasing sleep angle with time combined with decreasing activity can indicate worsening hear failure.

Treatment device 100 may detect heart rate variability, heart rate turbulence, or bradycardia. For example, medical condition sensors 110 may measure sympathetic and parasympathetic nervous system activity, and controller 105 may identify heart rate variability based on R-R intervals in ECG signals or a spectral analysis of heart rate variable frequencies. Information about these systems may be aggregated over time to identify trends.

In one embodiment, treatment device 100 is configured for self assessment entries by the subject. For example, a user interface that forms part of monitor 130 can receive quality of life information such as symptom information, body weight, and blood pressure by prompting the subject for these entries. Other self assessment entries that include quality of life information can be provided at selectable intervals, such as daily. Examples of these questions that prompt self assessment entries include: How do you feel today? How is your breathing today? Are you tired today? What is our weight today? What is your blood pressure today? What did you eat today? The subject may select from a standard list of responses, for example by indicating "worse" "the same" or "better." The subject may enter a number on a scale, for example from one to ten, or may enter measured values, for example of the subject's weight or blood pressure. In one embodiment, at least some of this information is sensed by sensors 110 or other devices, such as scales or blood pressure monitors. The subject can enter this information over the Internet, monitor 130, or a display on a battery charger unit given to patient, for example. Interfaces used for the entry of this information may be part of or remote from treatment device 100.

In one embodiment, wearable treatment device 100 includes biometric monitoring of the subject wearing treatment device 100 during initial risk assessments and during the course of treatment of a condition such as heart failure. Treatment device 100 monitors heart failure indicators and the onset of symptoms, and presents this information in a selectable and customizable form to a doctor in a periodic manner, at the doctor's choosing, or as an alert when a time sensitive condition may require quick treatment. Treatment device 100 can present this information in the form of aggregated reports that include trends with time of the subject's condition. In one embodiment, this information is aggregated in an omnibus quality of life score based on a plurality of sensed conditions. This aggregate score can be compared with a threshold value to indicate whether or when the subject requires treatment.

In one embodiment, to gather data under controlled conditions the subject undertakes physical activity, such as a six minute walk test that measures how far the subject can walk in six minutes. In this example, the subject wears treatment device 100 during the six minute walk test. Via monitor 130, treatment device 100 can guide or prompt the subject throughout the test, while protecting the subject from, for example, cardiac arrest by providing an external defibrillator. Medical condition sensors 110 (e.g., pulse oximeters) and activity sensors 135 such as pedometers can measure the subject's distance traveled, stride distance, respiration, heart rate, ECG, blood oxygen saturation, and recovery time before, during, and after the six minute walk test. The doctor can use this information to evaluate a treatment regimen or track the subject's progress. For example, the six minute walk test can be administered before and after changes to the subject's treatment regimen to evaluate the subject's progress and the efficacy of treatment. In one embodiment, the six minute walk test is modified to determine energy spent by the subject during the six minute walk, for example based on x, y, and z direction accelerometer measurements taken during the test. The subject can wear treatment device 100, and treatment device 100 can apply treatment to the subject, during the test.

In one embodiment, treatment device 100 tracks the subject's exercise regimen. For example, when the exercise is walking, cycling, or aerobic activity, treatment device 100 tracks duration, distance covered, heart rate, date, respiration rate, transthoracic impedance, walking angle, heart rate variability, time spent exercising, the subject's ECG, and post-exercise recovery time. Treatment device 100 can capture this information continuously during exercise and can present this information to a doctor for analysis and record keeping. In one embodiment, treatment device 100 alerts the subject that it is time to exercise at a determined date or time. Treatment device 100 may also identify a target heart rate (or range) and prompt the subject in real time to exercise with greater or lesser intensity in order to maintain a heart rate substantially at the target heart rate and to properly warm up and cool down before and after exercising. The target range can be adjusted based on information provided by sensors 110, 135.

Throughout the exercise regimen, treatment device 100 can monitor, record, and report information related to the subject's activity together with date and time information. Reports or summaries of this subject activity can be provided to a doctor, and can flag for the doctor's attention any conditions or changes that may have occurred during exercise.

Treatment device 100 may also act as a diet monitor that sets up and tracks the subject's eating habits. This information can be reported to a doctor. In one embodiment, treatment device 100 monitors a treatment regimen that includes special dietary guidelines, such as a low fat, low calorie, or low salt diet. The subject can enter information about the food the subject is eating in real time, via a user interface of monitor 130. In one embodiment, the user interface includes a bar code scanner to scan packaged food bar codes and retrieve their nutritional information from a database. In some embodiments, treatment device 100 monitors the subject's diet and weight in parallel and adjusts a recommended diet regimen of the subject to adjust or maintain the subject's weight. For example, treatment device 100 can normalize food intake to overall subject energy, deduced by controller 105 from accelerometer readings, over a period of time to identify a diet regimen.

Further examples of the information sensed and evaluated by the components of wearable treatment device 100 include the following:

Subject Movement During Arrhythmia

Activity sensors 135, such as an accelerometer can be used to determine a subject's body state during the detection of an arrhythmia. They can also be used to detect if a mechanically noisy environment is the cause of erroneous arrhythmia detection.

Subject Movement Used in the Confidence Algorithm Factor

In one embodiment, a confidence algorithm, which can be influenced by many inputs including the subject's body state as determined by activity sensors 135, is used to determine if a subject's heart arrhythmias requires defibrillation by treatment device 100.

In one embodiment, cardiac treatment is not required if the subject is conscious and occurs only when the subject is unconscious. By using activity sensors 135 the subject body state can be monitored. In one embodiment, when there has been no change in subject body state for a period of time as detected by activity sensors 135 then there will be an increased confidence of the algorithm that the subject is unconscious. For example, if a change in subject body state is detected by activity sensors 135, such as an accelerometer, then there will be a decreased confidence of the algorithm that the subject is unconscious. Treatment device 100 can adjust the treatment regimen to, for example, hasten the application of treatment if a high level of confidence exists that the subject is unconscious. If subject motion is detected while other sensors 110 and algorithms processed by controller 105 indicate that a treatable rhythm is present, treatment delivery can be delayed to provide the subject additional time to respond to system messaging.

False Arrhythmia Detection Due to Physical Motion

Controller 105 can detect a false arrhythmia due to physical motion. For example, sensors 110 or wire 125 can move against the body or clothing, creating false deviations in the subject's ECG. If an arrhythmia is detected and vibration or high subject/equipment acceleration is detected, then the subject can be alerted to this condition. Monitor 130 or an alarm module can notify the subject. This information may also be applied to the treatment confidence algorithm thereby causing a decrease in confidence given that the physical motion can cause a false positive detection. Use of activity sensors 135 can reduce undesired treatment of false arrhythmias.

Correlation of ECG Artifact with Belt Motion

Motion of the belt or other treatment device 100 component may cause interference with ECG signal pickup and possible false detections. The signals obtained from activity sensors 135 or other sensors 110 can be correlated with an ECG signal to determine if ECG signal contamination exists. The quality of the correlation can be used by controller 105 as an additional confidence factor in the arrhythmia detection algorithm. If an arrhythmia is detected and there is a high degree of correlation between the ECG signal and a signal from activity sensor 135, the confidence in the arrhythmia detection can be reduced. No signal correlation indicates increased confidence that the arrhythmia detection is accurate.

Treatment Verification

Activity sensors 135, such as accelerometers may also be used to verify that a treatment has been applied by detecting sudden movements or muscle spasms in the subject immediately following the treatment. Often after defibrillation the subject's muscles spasm from the energy pulse. The muscle spasm can cause detectable movements on activity sensors 135 similar to convulsing.

Detection of Bystanders/Unsuccessful Defibrillation

Post shock motion of the subject after several unsuccessful defibrillation attempts may indicate the presence of bystanders. The bystanders could be rescue personnel such as an EMT. In this case monitor 130 or an associated alarm module can generate audio or visual alarms or voice messages to inform the bystander of the equipment and treatment status. Controller 105 can adjust the timing of additional shocks (for example by delaying or canceling them) to prevent a shock to the bystanders or rescue personnel.

Post Shock Motion Detection

When a shock is delivered, the subject may move suddenly and then return to a state where there is a lack of motion. If no further motion is detected, controller 105 can determine with a high confidence level that the arrhythmia is still present. This information can be used by controller 105 as an additional post-shock confidence factor for the detection algorithm and that a continuing cardiac condition exists. If post-shock motion continues or if the subject body position changes from a horizontal to vertical position, controller 105 can determine that there is high confidence that the defibrillation was successful and additional shocks or other treatment can be delayed. Based on post shock motion, treatment device 100 can also detect and control pacing of the subject.

Belt Quality Feedback

Treatment device 100 may include a belt for proper positioning on the subject and to house treatment device 100 components. Overall belt quality can be examined by gathering data using activity sensors 135 during certain failure states such as sensor 110 fall-off and treatment electrode 115 fall-off detection.

Reduce Electrode and Therapy Pad Fall-Offs

If one of sensors 110 or treatment electrodes 115 fall off of the subject, controller 105 can record the subject's body state during the fall-off event based on information from sensors 110, 135 or information input by the subject via a user interface. Subject positions include sitting up, lying down; left side, right side. If controller 105 identifies vibration or the subject falling then that information can be recorded and evaluated by controller 105 since it might be the cause of the falloff event. Over time, controller 105 can use this information to determine positions that may tend to cause fall-offs of treatment device 100 components. This information can then be used to improve the belt design reducing and possibly eliminating the fall-offs in those certain activities or positions. This information can also be used to train the subject and those assisting the subject as to how to wear and use treatment device 100 and its components, as well as to establish instructions for future use of treatment device 100. An example would be if post analysis of data over a several month period of time shows that 75% of ECG fall-offs occur when the subject is laying on their left side then the belt design on the left side could be examined to determine what might be making it susceptible to fall-offs in that subject position.

Provide Recommendations to Subjects

Activity sensor 135 data collected over time could also be used to inform subjects of body states that tend to be more comfortable. Subjects who have worn the device for an extended time will most likely have experimented with different positions (sleeping positions, sitting positions, etc.) and will tend to use the most comfortable ones. This data can be provided to controller 105, stored, and used to improve the belt for the other positions and also provide recommendations to new subjects.

Improve Belt Comfort

Data collected by sensors 110 during subject use can be used to improve the comfort of the treatment device 100 when worn by studying subject sleep habits, or habits during other selected activities. For example, if 80% of the subjects tend to sleep on their right side then the assumption can be made that something about the belt makes it less comfortable for the subjects to lie on their left side. With this information controller 105 can determine what about that position causes the belt to be uncomfortable and engineering can be performed to improve treatment device 100 comfort.

Belt Self Diagnostics

Self diagnostics may also be provided such as a Belt Node Tactile Stimulator (vibration/acceleration) self test. For example, treatment device 100 may include a tactile stimulator or other subject notification device. The tactile stimulator may include a motor with an unbalancing weight on its shaft. When the motor is on, it causes the belt to vibrate much like a cell-phone in vibration mode. When the tactile stimulator is activated, an activity sensor 135, such as an accelerometer in node 120 can detect vibrations from the tactile stimulator to verify that node 120 is vibrating and that the tactile stimulator is working. The tactile stimulator can be housed in node 120, with monitor 130, or the alarm module.

Subject Notification of Physical Events

Controller 105 can use activity sensor 135 information to provide feedback to the subject regarding mechanical events, or to adjust audio volume outputs of the alarm module or monitor 130 based on the current state of the subject.

Equipment Abuse Notification

If certain mechanical conditions that may lead to equipment damage such as mechanical shock or vibration are detected by activity sensors 135 then the controller 105 can instruct monitor 130 or the alarm module to notify the subject of such conditions and advise the subject of the condition.

If monitor 130 or belt is dropped, or if they are hit with some other object causing a force greater than a predefined acceptable force, then monitor 130 or the alarm module can provide an audio, visual, or haptic indication to the subject that the event has occurred and warn against allowing such an event to occur again.

If continuous vibration above a certain predefined acceptable threshold is detected for a period of time, then monitor 130 or the alarm module may also provide a warning to the subject. Such vibration could lead to sensor 110 or treatment electrode 115 fall-off, or even cause false arrhythmia detection if enough physical motion is applied to the sensors 110, treatment electrodes 115, wires 125, or other components.

Adjust Device Alarm Volumes

If information from activity sensors 135 indicates that the subject's body state is unchanged for a period of time, and the subject is either lying or sitting down then controller 105 can determine that the subject is sleeping and can increase the audio volume output of any audio message if necessary to awaken the subject. Controller 105 may also enable the tactile stimulator to awaken the subject in the event of a critical audio message.

Adjust Display Rotation

Information from activity sensors 135 can be used by controller 105 to determine the proper position of monitor 130 to deliver a visual message to the subject or for initial subject setup by care givers. For visual messages to the subject, since monitor 130 can be positioned approximately at the subject's mid section, the display of information by monitor 130 may appear upside down (rotated 180 degrees) with respect to monitor 130. However, during setup, when the subject is fitted with treatment device 100 and when its components are positioned, monitor 130 could be held right side up in front of the skilled personnel. As a result, the display would be right side up.

Detect Equipment Abuse

Controller 105 can detect abuse of treatment device 100 and its components during use as well as during shipping. This abuse can be determined by parameters such as number of times dropped and intensity. Detection of abuse can trigger such actions as internal diagnostics, auto download, and equipment service recommendations.

Equipment Drop Detection

If activity sensors 135 detect a mechanical shock, for example to monitor 130 above a pre-determined acceptable threshold, then controller 105 can identify and record a drop event. Other parameters such as date/time stamp and current operating mode can be identified and recorded as well. The date/time stamp can allow correlation between monitor 130 location and the damaging event allowing further information to be obtained using the carrier tracking numbers if such damage occurred during shipping.

If it is not during shipping and is during use of treatment device 100 by the subject, and there is some form of treatment device 100 malfunction after the drop then that could be tied to the root cause of the equipment failure. Such information could be used to advise subjects of the types of mechanical shocks that may damage the equipment or components of treatment device 100. It also may be used to improve the robustness of the equipment to survive such forces in the future.

Equipment Service Recommendation

If activity sensors 135 records a mechanical shock above a predefined acceptable threshold, or if a predefined acceptable number of mechanical shocks have occurred, monitor 130 can display a message indicating that the equipment should be serviced. Controller 105 can also, during the next download, notify the manufacturer that treatment device 100 should be serviced.

Internal Diagnostics

Logic devices that are part of activity sensor 135, monitor 130, or node 120 may constitute at least part of controller 105. If activity sensor 135 does detect an excessive mechanical shock on the belt or monitor 130 then controller 105 may initiate internal self-diagnostics. Activity sensor 135, monitor 130, and node 120 may include circuitry to allow most of its components to be tested with self diagnostics.

Auto Download to Manufacturer

If there is a significant mechanical shock to treatment device 100 components or equipment such as the belt or monitor 130, then controller 105 may communicate with the manufacturer via a communications network to request service.

Monitor Subject Activity Over Time

Data provided by activity sensor 135 or medical condition sensors 110 can be measured and stored over time to study subject activity. Subject activity data can be used to provide feedback to doctors about a subject's specific condition.

Subject Activity Data and Treatment

After applying treatment, subject activity data taken before, up to, and including the event can be downloaded from treatment device 100 to a remote data storage unit. This information can also be recorded locally at treatment device 100. This data can be collected among a plurality of subjects and used to make correlations between subject activity derived from sensors 110 and the probability of a cardiac event or other condition that requires treatment occurring. These correlations can be used to take precautionary measures with subjects who have similar activities as those who had past treatment events.

Subject Activity Data and Doctor Feedback

Subject activity data can be used over a period of time by doctors or data evaluation systems to determine if proper subject activity levels are met. For example, a doctor can analyze the data to determine that there is low subject activity, or that the subject is performing recommended exercises. The doctor can also monitor the subject's real time activity level and corresponding heart rate data. Subjects who are experiencing congestive heart failure can be monitored for physical activity and at rest body position. Gradual reduction in subject activity indicated by lack of motion can indicate a worsening of the congestive heart failure condition. Body position at rest can also indicate subject deterioration if body position at rest is primarily vertical since congestive heart failure subjects may have difficulty resting in a horizontal position.

Figure 6:
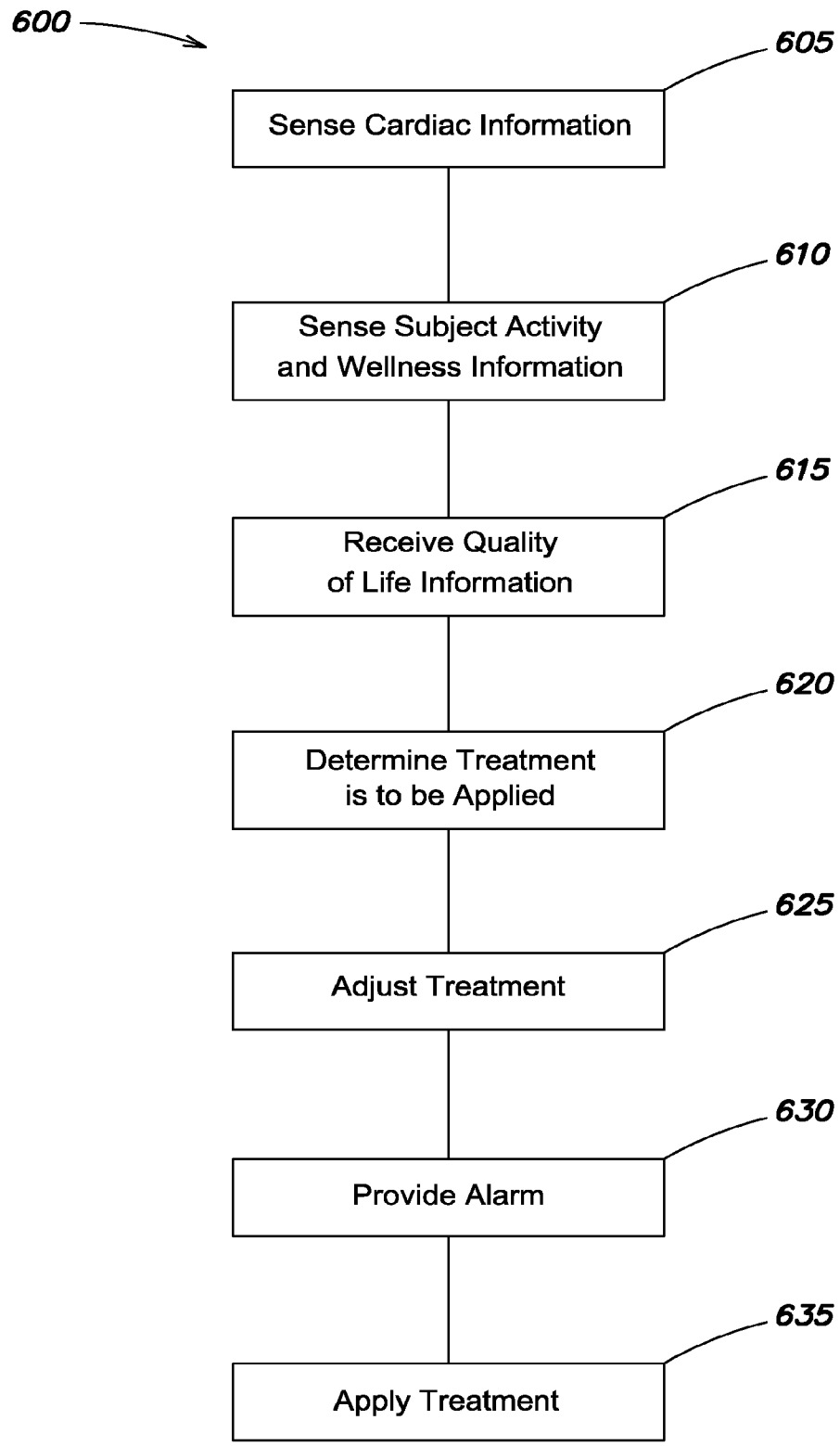
FIG. 6 depicts a flow chart for a method of monitoring and treating a subject in accordance with an embodiment.

FIG. 6 depicts a flow chart for a method 600 of monitoring and treating a subject. In one embodiment, method 600 includes an act of sensing cardiac information of a subject (ACT 605). For example, sensing cardiac information (ACT 605) may include detecting ECG (electrocardiogram) signals or other information related to electrical or mechanical activity of the subject's heart. In one embodiment, dry external electrodes are configured external to the subject to sense (ACT 605) cardiac information. Internal electrodes may be used as well. Sensors used to sense (ACT 605) cardiac information can be part of a wearable subject treatment device that includes an external defibrillator. In one embodiment, sensing cardiac information (ACT 605) includes sensing information indicative of heart failure or other medical conditions.

In one embodiment, method 600 includes the act of sensing at least one of subject activity and wellness information (ACT 610). For example, internal or external sensors proximate to the subject's body can sense (ACT 610) pulse, breathing, temperature, blood pressure, or fatigue information, for example. In one embodiment, sensing activity and wellness information (ACT 610) includes detecting subject movement, lack thereof, position, or orientation. Sensing activity or wellness information (ACT 610) may include detecting tangible medical or physical condition or information indicative of a subject's overall health, as well as changes in health-related measurements or conditions with time.

Method 600 may also include at least one act of receiving quality of life information (ACT 615). The quality of life information may be received from the subject, or on the subject's behalf from a physician or someone acting on the subject's behalf. In one embodiment, quality of life information is received (ACT 615) by a user interface of a wearable treatment device. For example, the quality of life information may be received (ACT 615) via direct manual entry into the user interface, or remotely via one or more wired or wireless networks. Receiving quality of life information (ACT 615) may include receiving information about the subject's lifestyle, such as dietary, activity, or exercise habits, when the subject last took a particular action, or information about how the subject feels.

In one embodiment, method 600 includes acts of determining whether or not treatment is to be applied (ACT 620) and adjusting the determined treatment (ACT 625). For example, treatment (e.g., an electric shock) can be determined to be applied (ACT 620) based on the detected (ACT 605) cardiac information. In this example, sensed (ACT 605) cardiac information may indicate that the subject is experiencing a cardiac event and in need of pacing or defibrillation. Adjusting the treatment (ACT 625) may include time shifting the application of the treatment, or delaying application of the treatment pending confirmation of the subject's condition, based on the subject's sensed (ACT 610) activity and wellness information. For example, method 600 can determine (ACT 620) that treatment is not to be applied due to a high heart beat, when sensed (ACT 610) subject activity and wellness information indicates that the subject is intensely exercising, and that this may be the cause of the elevated heart beat. In this example, application of pacing or other treatment can be delayed (ACT 620) until it is determined that the subject is no longer exercising yet still has an elevated heart rate.

In one embodiment, method 600 includes an act of providing an alarm (ACT 630). For example, an alarm can be provided (ACT 630) by alerting the subject or other person of treatment. The alarm may be audio, visual, haptic, or combinations thereof, and can alert the subject and others in the vicinity of the subject of a treatment regimen. In one embodiment, providing the alarm (ACT 630) includes alerting a doctor or health care provider that treatment has, is, or will be applied to a subject where the doctor is located remotely from the subject. For example, the alarm may be provided (ACT 630) when the subject is on the street, or at home. In this example, the alarm can be provided remotely via wired or wireless communications through a communications network to the doctor who may be present in a hospital or office.

In some embodiments, providing the alarm (ACT 630) includes alerting the subject or other person of a treatment regimen subsequent to sensing the subject's cardiac information (ACT 605). Providing the alarm (ACT 630) may also include alerting the subject or other person of a treatment regimen prior to an act of applying treatment to the subject (ACT 635). In one embodiment, applying treatment to the subject (ACT 635) includes applying an electrical shock or current to the subject as part of a defibrillation or pacing treatment regimen. In some embodiments, applying treatment (ACT 635) occurs subsequent to the act of alerting the subject or another person that treatment has been applied, is being applied, or will be applied.

Figure 7:
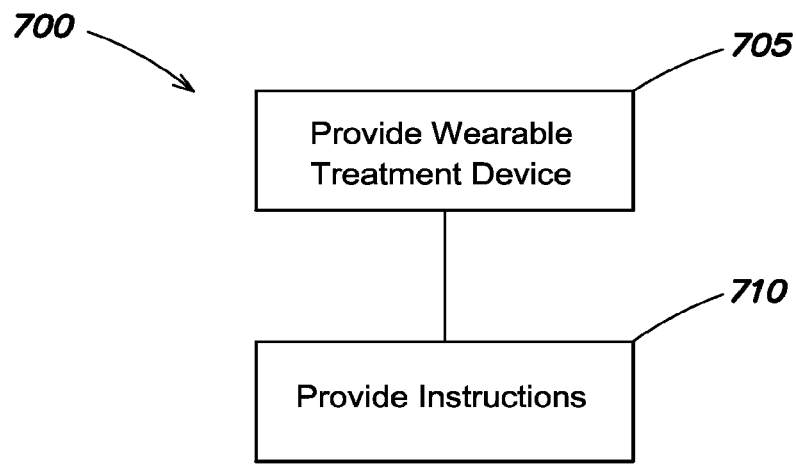
FIG. 7 depicts a flow chart for a method of monitoring and treating a subject in accordance with an embodiment.

FIG. 7 depicts a flow chart for a method 700 of monitoring and treating a subject. In one embodiment, method 700 includes an act of providing the wearable treatment device (ACT 705). For example, providing the device (ACT 705) may include providing a garment in the general form of a vest or shirt that may include at least one strap, belt, pocket or receptacle. In one embodiment, providing the wearable treatment device (ACT 705) includes providing a device that includes a cardiac sensing electrode to detect cardiac information (e.g., ECG) of the subject, and a treatment electrode to apply electric current to the subject as part of, for example, a defibrillation or pacing treatment. Providing the device (ACT 705) may also include providing a user interface to receive quality of life information from the subject. This may include factual data about the subject's lifestyle, as well as the subject's opinion as to how the subject feels or the subject's health. Providing the device (ACT 705) may also include providing a garment with an activity sensor, such as one or more motion sensors or accelerometers to detect subject activity and wellness information indicative of a general wellness of the subject.

In one embodiment, providing the device (ACT 705) includes providing a controller. The controller communicates with the cardiac sensing electrode, the treatment electrode, the user interface, and the sensor to receive the detected cardiac information, the quality of life information, and the detected subject activity and wellness information. The controller can also determine that treatment is to be applied to the body of the subject based upon the detected cardiac information, and can adjust the treatment based on at least one of the detected subject activity and wellness information and the quality of life information. In one embodiment, providing the device (ACT 705) includes providing an alarm module. The alarm module can provide an alarm to indicate treatment has, is, or will be applied to the body of the subject.

In one embodiment, method 700 includes an act of providing instructions (ACT 710). This may include providing instructions to operate the wearable treatment device. For example, providing instructions (ACT 710) can include providing at least one instruction to position at least one of the cardiac sensing electrode, the therapy electrode, and the activity sensor on the subject, and any other device components on the subject. Providing instructions (ACT 710) may also include providing instructions to wear or position the wearable treatment device or any of its components on the subject.

Figure 8:
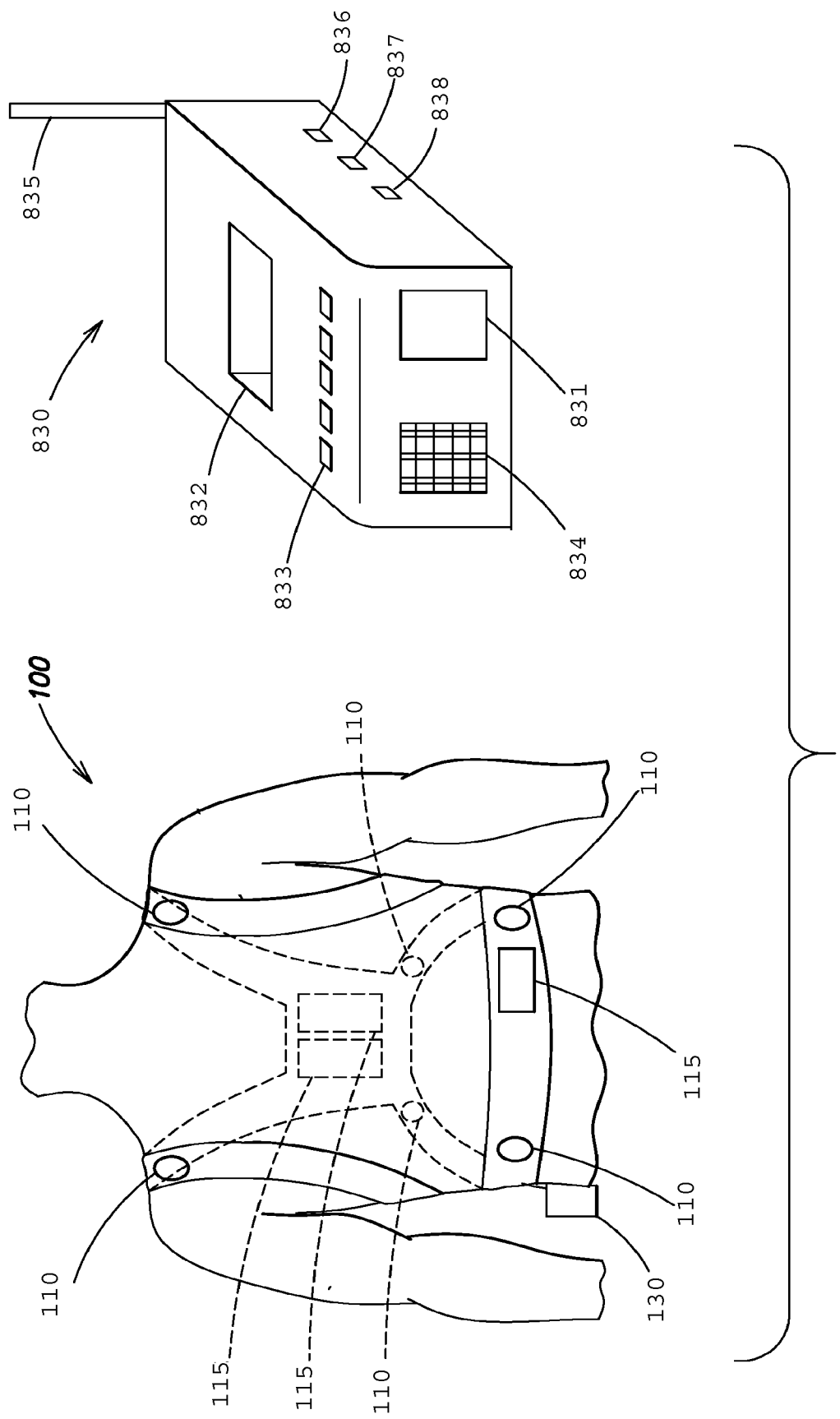
FIG. 8 illustrates a wearable medical device, such as a wearable defibrillator and an associated base unit.

As shown in FIG. 8, the wearable treatment device 100 may be associated with a base unit 830. For example, in the LifeVest® wearable cardioverter defibrillator, a base unit 830 is provided that is capable of performing a number of different functions. One of the functions performed by the base unit 830 is to charge an auxiliary battery that is used to provide power to the wearable treatment device. The Life-Vest® wearable cardioverter defibrillator is provided with two batteries, such that one of the batteries is recharged while the other is providing power to the device. When the battery that is providing power to the device needs recharging, it is swapped with the auxiliary battery, and recharged, with this cycle being repeated throughout the duration of patient usage. Another of the functions performed by the base unit 830 is to store and/or communicate information received from the wearable treatment device over a wired or wireless communication network. For example, information relating to the patient's medical condition over a period of time may be communicated by the base unit 830 to a medical service provider, such as a doctor, so that the doctor may remotely monitor the patient's medical condition. The information received by the base unit 830 may be communicated over the network shortly after it is received by the base unit 830, or alternatively, may be stored in a memory of the base unit 830 and communicated over the network at a later time. The information that is communicated by the base unit 830 may be retained in the memory of the base unit.

The base unit 830 includes a visual display 831 that can communicate visual messages to the patient or a bystander, an audio output device 834, such as a loudspeaker, that can communicate audible messages to the patient or a bystander, and a plurality of buttons 833 by which the patient or a bystander can communicate with the base unit 830. In certain embodiments, the visual display 831 may include a touch screen display, such that the patient or a bystander may also communicate with the base unit via the visual display 831. The base unit 830 includes at least one charging bay 832 to receive a rechargeable auxiliary battery, such as a three cell 2200 mAh lithium ion battery pack, that can be used to provide power to the wearable treatment device 100. The base unit 830 also includes several different communication interfaces including: a device communication interface 838 to receive information from the wearable treatment device, a telephone network interface 836 to communicate, via a telephone network, the information received from the wearable treatment device, and a network interface 837 to communicate, via a wired network connection, the information received from the wearable treatment device. In certain embodiments, the base unit 830 also includes an antenna 835 that can wirelessly communicate the information received from the wearable treatment device via a cellular (e.g., 2G, 3G, and 4G) network.

As should be appreciated by those skilled in the art, there are times when it would be desirable to re-configure the wearable treatment device 100. For example, it may be desirable to re-configure the wearable treatment device to upgrade the wearable treatment device to a new revision level of software, where that new revision level of software incorporates additional safeguards, improved cardiac arrhythmia detection and/or treatment algorithms, or different or additional reporting functions. In other instances, there may be no need to upgrade the revision level of software of the wearable treatment device, but it may be desirable to adjust the operational settings or control options of the wearable treatment device to better reflect the subject's current medical state, where that state may have changed since the time the wearable treatment device was initially configured.

As should be appreciated by those skilled in the art, it would be desirable to have the ability to configure (or reconfigure) the wearable treatment device remotely, such that the subject (referred to hereinafter as the patient) need not return the wearable treatment device to the manufacturer, or return to the doctor's office, or other location where the device was previously configured. However, as should also be appreciated by those skilled in the art, remotely configuring or reconfiguring a device, such as a wearable monitoring and/or treatment device such as a wearable defibrillator presents unique challenges, not the least of which include patient safety and patient privacy.

When prescribing a patient with a wearable monitoring and/or treatment device such as a wearable defibrillator, certain variables typically need to be entered into the device, such as the patient's name, clinical center, and defibrillation settings such as rate thresholds and energy settings. Customarily, to program the device for the patient, one needs to be able to enter a programming mode, and then enter or change the affected settings. The person doing the programming needs to be sure to enter the settings correctly, because this affects the safe and effective operation of the device. Entering the wrong variables can affect the patient's safety and the proper operation of the device. Typically programming is done by a trained, skilled individual, and not by a casual user or the patient. In fact, the device may be configured to lock out anyone from changing the programming settings by accident. Programming also is typically done directly on the device, requiring the programming to be done in person, and typically at the time of the fitting, when the patient is being given the device to wear.

As noted above, one of the problems that can arise is the need to change the programming at a later date. For example, in a wearable monitoring and/or treatment device, such as a wearable defibrillator, if the patient experiences a number of alarms due to the patient's normal heart rate being too close to the alarm rate threshold for ventricular tachycardia or ventricular fibrillation, the patient's physician may decide to raise the alarm rate thresholds. In other instances, there may be additional device options that the patient's physician may want to enable and set after the initial fitting. For example, the device may have features that make it particularly valuable for monitoring the patient's heart and other biometrics that can provide information that is useful in the treatment of heart disease or failure. For that reason, it may be desirable to enable these options, and change their parameters, sometime after the initial fitting of the device.

Where the wearable monitoring and/or treatment device is a wearable defibrillator, such as the LifeVest® wearable cardioverter defibrillator that includes multiple ECG sensing electrodes, it may be desirable to select a particular pairing of ECG sensing electrodes for use in monitoring the patient. For example, the LifeVest® wearable cardioverter defibrillator obtains two channels of ECG signal from four ECG sensors positioned around the circumference of the patient's electrode belt. The two channels are side-to-side (SS) and front-to-back (FB). The lead preference option allows one to select the primary channel used to obtain the ECG signal used for the arrhythmia detection algorithm. The other channel will be used as a secondary signal, in the event of noise or dropout of the primary channel. In some patients, the signal obtained from one channel is superior to the signal obtained from the other channel. One signal is typically stronger, and perhaps with more pronounced R-waves. If a patient is experiencing problems with a weak signal, or if the patient has an ECG that is "fooling" the detection algorithm by causing it to double-count R-waves, it is desirable to change the lead preference to the other channel. This requires a programming change.

Conventionally, the only way to change any of the programmed settings is to send a person to the patient's home that is skilled in programming the device. Another alternative is to have the patient come into the physician's office to have the device reprogrammed. Still another alternative is to send the patient a different device that is programmed with the new settings. All of these methods are fraught with the problems of taking time, costing money, and inconveniencing the patient. Also, all of these methods introduce delays into the process, which may put the patient at an increased level of risk until the device is reprogrammed. In these cases, where it is desirable to change the programming or options of the device after the initial fitting, it would be an advantage to be able to remotely program the device without having to send a programmer to the patient's home, or having the patient come into the physician's office to have the device reprogrammed.

Device Update System

In accordance with another aspect of the present invention, a system and method is provided for permitting a wearable medical monitoring and/or treatment device, such as a wearable defibrillator, to be configured or re-configured from a location that is remote from the wearable device itself. Thus, a user at a remote location may enter sensitive programming information without actually being in the presence of the device itself. To enable such functionality, a secure communication mechanism is provided that interfaces between the wearable monitoring and/or treatment device and the remote location. This secure communication provides all the information that the device needs to tailor any of the device's settings or other configuration information (e.g., monitoring settings, treatment settings, reporting settings, etc.) to a specific patient.

It should be appreciated that any such communication mechanism should have robust security and authenticity. For example, before updating the device, the remote communication mechanism should verify that it is communicating with the correct device that is being worn by a specific patient. During the updating process, it is important that the communication link ward off any attempts at corruption in order to maintain data integrity and patient privacy. After updating the device, the remote communication mechanism should verify that the device has been updated correctly, and has not been corrupted.

According to various embodiments disclosed herein, the device includes a unique serial number and patient unique identification information that may be stored in a memory of the device. In at least one of these embodiments, the device will not accept an enable message (a message to initiate a configuration sequence, such as an update session request which is described further below) without the device being enabled by a specific patient action. Further in this embodiment, a random code is generated by the device only after a properly formed enable message has been received. The sequencing of message transmission and delivery can be aborted based upon timeout or mal-formed message sequence. It is to be appreciated that execution of device monitoring and/or device treatment functions remains active during the configuration sequence/update session. In addition, it is to be appreciated that a configuration sequence may be aborted if a treatment function becomes necessary during the execution of the configuration sequence.

Figure 9:
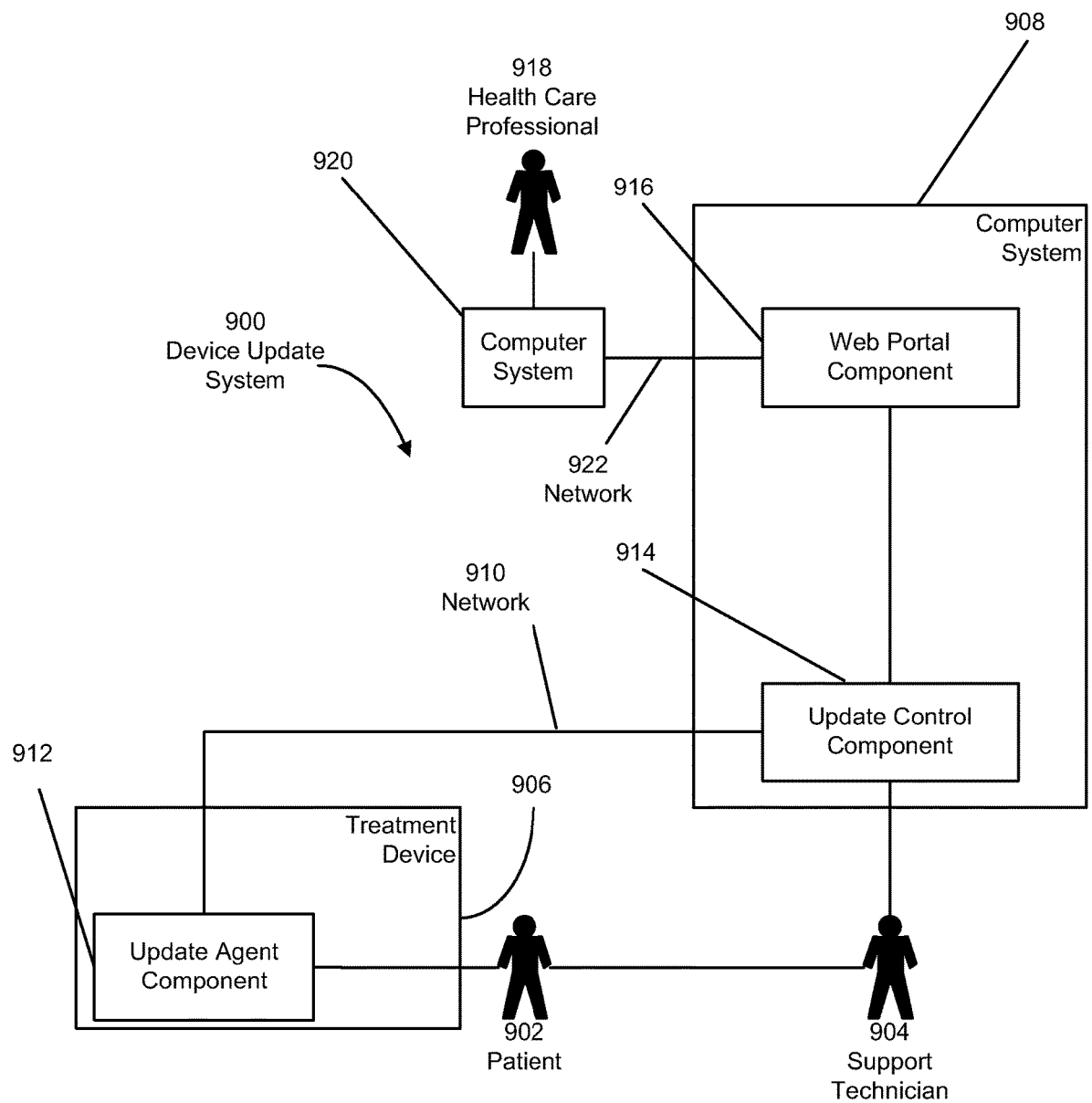
FIG. 9 is a block diagram including an example system for updating a treatment device.

To implement the update functionality described herein, various embodiments utilize one or more ambulatory medical treatment devices in conjunction with one or more computer systems. FIG. 9 illustrates one of these embodiments, a device update system 900. As shown, FIG. 9 includes a patient 902, a support technician 904, a health care professional 918, an ambulatory medical treatment device 906 (which is also referred to simply as a treatment device 906 herein), computer systems 908 and 920, and communication networks 910 and 922. The computer system 908 includes an update control component 914 and a web portal component 916. The treatment device 906 includes an update agent component 912. The treatment device 906 may include any programmable device (a device including memory for storing data and at least one processor coupled to the memory) configured to administer therapeutic measures to mobile patients, such as the treatment devices described above with reference to FIGS. 1-4 and 8. The computer system 908 may include one or more computer systems, such as the computer system described below with reference to FIG. 10.

As depicted in FIG. 9, the computer system 908 and the treatment device 906 exchange (i.e. send or receive) information via the network 910. Similarly, the computer system 920 and the computer system 908 exchange information via the network 922. The network 910 or the network 922 may include any communication network through which programmable devices may exchange information. For example, the network 910 or the network 922 may be a public network, such as the internet, and may include other public or private networks such as LANs, WANs, extranets, intranets, and cloud computing systems. The network 910 or the network 922 may also include cellular networks such as CMDA, EvDO, GSM, and iDEN networks. Although the network 910 and the network 922 are illustrated as distinct networks in FIG. 9, embodiments disclosed herein are not limited to two distinct networks. The network 910 and the network 922 may be a unified, connected network or may include other networks without departing from the scope of the embodiments disclosed herein.

In at least one example, an authorized person, such as a health care professional 918 treating the patient 902 via the treatment device 906, prescribes changes to the parameters of the treatment device 906 or seeks additional information from the patient 902 via the treatment device 906. The parameters of the treatment device may include a treatment plan, settings used to alter monitoring and treatment performance, rehabilitation protocol, and the like. The additional information sought by the health care professional may include answers to direct questions, as may be presented in a health survey, or data gathered while the patient performs activities instructed via the treatment device 906. For example, the treatment device 906 may ask the patient to perform a walk test as described above while the treatment device 906 records data descriptive of the physiological processes occurring within the patient 902 as well as task performance. In some embodiments, the treatment device may both gather information via a combination of these approaches (i.e., direct questioning and physiological monitoring).

To alter parameters of the treatment device 906 or initiate information collection via the treatment device 906, the health care professional 918 may instruct the support technician 904 to alter the configuration information of the treatment device by conducting an update process. In some embodiments, the health care professional 918 may communicate these instructions via the web portal component 916. In these embodiments, the web portal component 916 is a secure, web based, storage and retrieval system for information regarding wearable medical monitoring and/or treatment devices, such as a wearable defibrillator. Using the web portal 916, medical professionals (e.g., the health care professional 918) can access patient data for patients (e.g. the patient 902) wearing such treatment devices (e.g., the treatment device 906) and monitor the patient's medical condition, set up alerts and notifications, and the like.

In embodiment illustrated in FIG. 9, the web portal component 916 serves a secure user interface to the health care professional 918 via the network 922 and the computer system 920. The computer system 920 renders the user interface and exchanges information descriptive of instructions to alter the configuration of the treatment device 906 with the health care professional 918. In response to receiving this information, the web portal 916 processes the information and provides the instructions to the support technician 904. To exchange information with the health care professional 918, the web portal component 916 may employ a variety of metaphors and user interface elements. Examples of user interface elements served by the web portal component 916 and rendered by the computer system 920 are described further below with reference to FIGS. 12 and 14.

Figure 13:
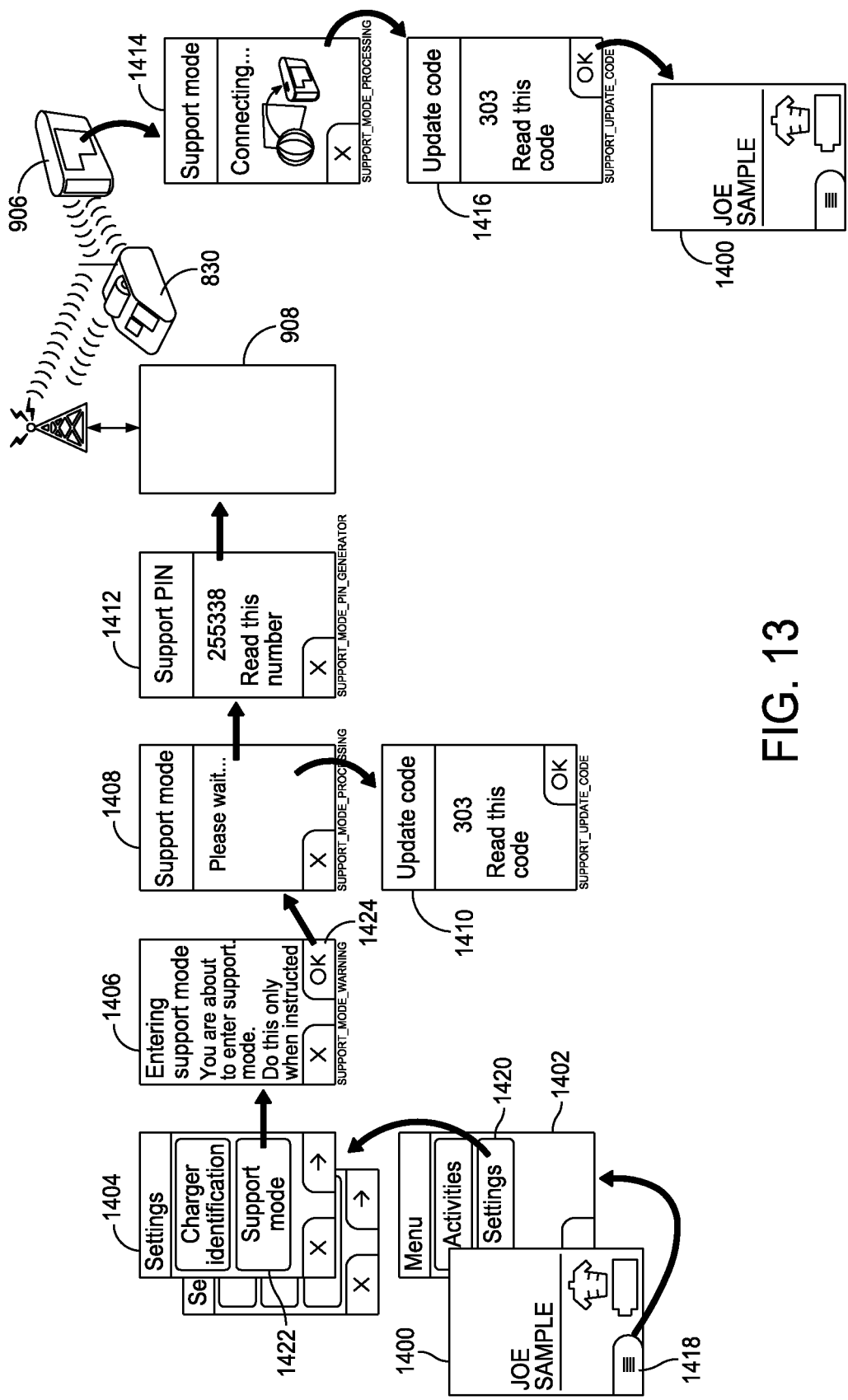
FIG. 13 is pictorial representation of certain screens that may be displayed on a display of a monitor of a wearable medical monitoring and/or treatment device during execution of an exemplary method of configuring or reconfiguring the wearable medical monitoring and/or treatment device.
Figure 14:
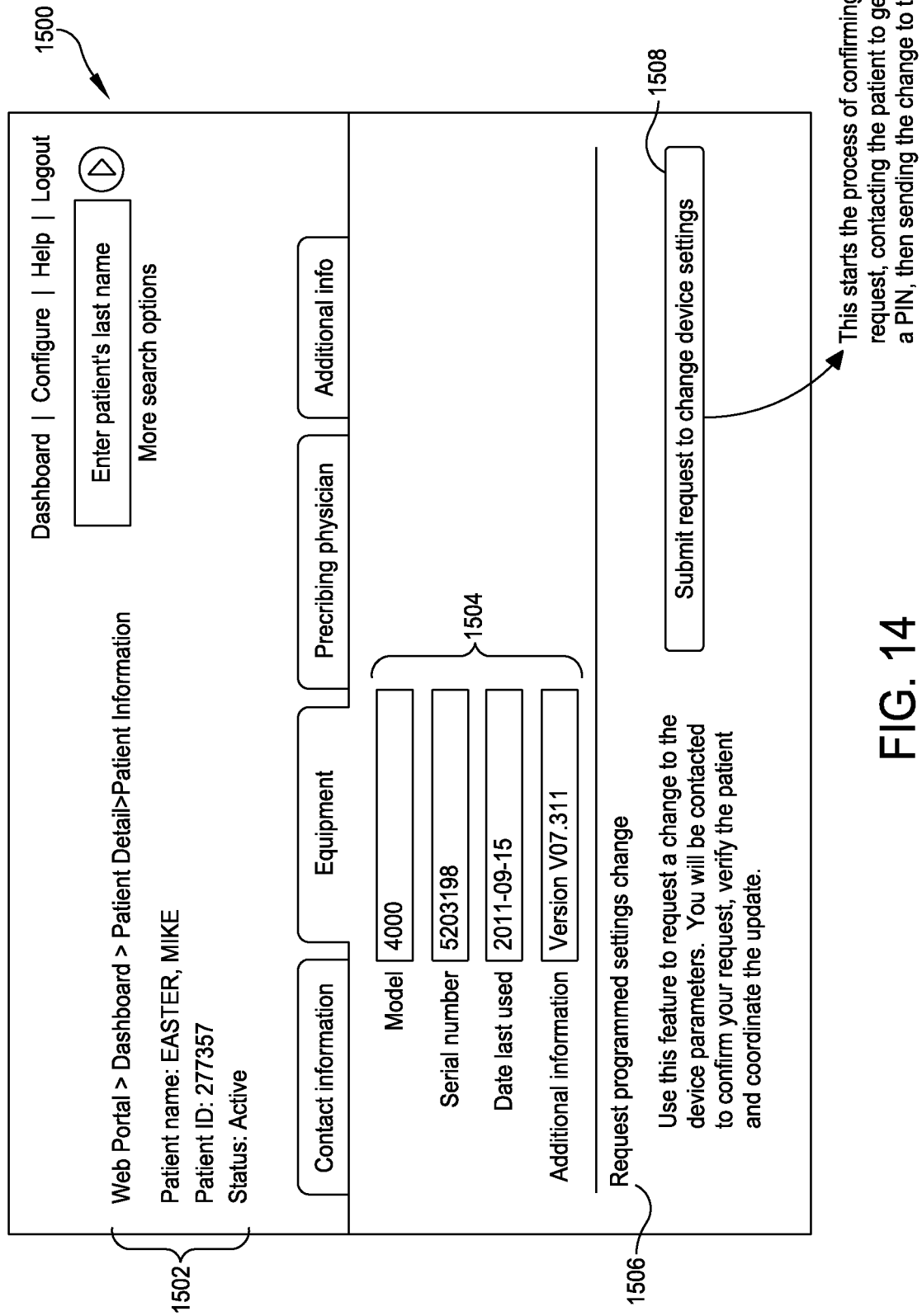
FIG. 14 is an illustration of a user interface screen that may be displayed by the monitor of the wearable medical monitoring and/or treatment device to permit remote configuration or reconfiguration of the device.
Figure 15:
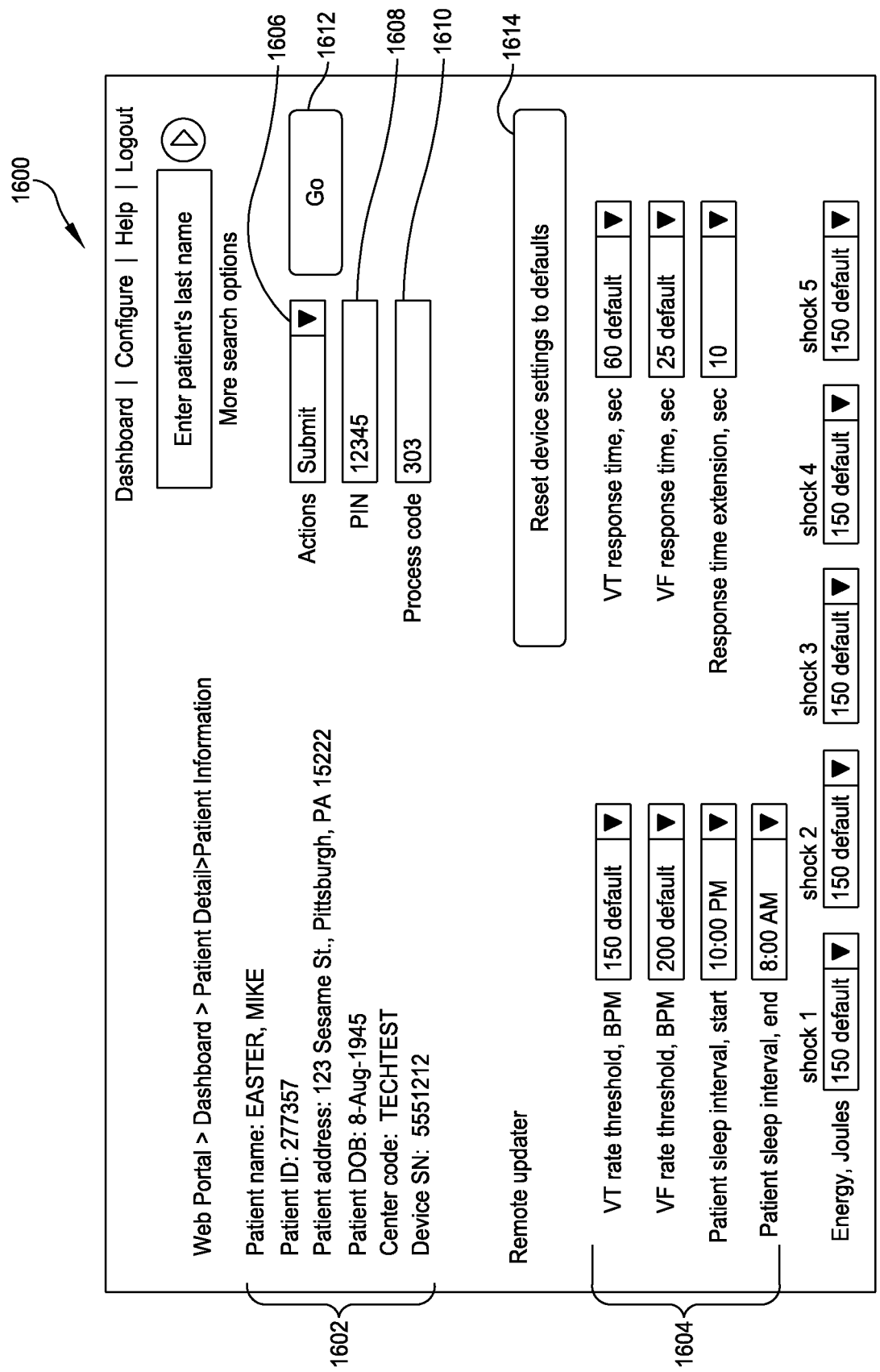
FIG. 15 is an illustration of a user interface screen that may be displayed on a computer display screen used by a support representative to reconfigure a wearable medical monitoring and/or treatment device remotely.

In some embodiments, and as illustrated in FIG. 9, the computer system 908 executes the update control component 914. The update control component 914 is configured to exchange information with the support technician 904 and the update agent component 912 during execution of the processes described below with reference to FIGS. 11-13. The information processed by the update control component 914 may include requests to change configuration information, requests for authorization, requests for update sessions, requests for authentication, requests to initiate updates, requests to process acknowledgments, and the like. To exchange information with the update agent component 912, the update control component 914 generates and transmits messages to the update agent component 912 that subscribe to a protocol supported by the update agent component 912. To exchange information with the support technician 904, the update control component 914 may employ a variety of metaphors and user interface elements. For example, in one embodiment, the update control component 914 includes a support interface component with screens and other elements that, when selected by the support technician 904, prompt the support technician 904 to enter a request to change parameters of the treatment device 906. FIGS. 14 and 15 illustrate screens and other elements in accord with this example.

As illustrated in FIG. 9, the treatment device 906 executes an update agent component 912. The update agent component 912 is configured to exchange information with the patient 902 and the update control component 914 during execution of the processes described below with reference to FIGS. 11-13. The information processed by the update agent component 912 may include requests to enter support mode, requests to provide update session identifiers, requests to execute updates, and the like. To exchange information with the update control component 914, the update agent component 912 generates and transmits messages to the update control component 914 that subscribe to a protocol supported by the update control component 914. To exchange information with the patient 902, the update agent component 912 may employ a variety of metaphors and user interface elements. For example, in one embodiment, the update agent component 912 provides screens with elements that, when selected by the patient 902, prompt the patient 902 to enter a request for an update session. FIG. 13 illustrates screens in accord with this example. In at least one embodiment, the update agent component 912 includes a user interface component and a system interface component. In this embodiment, the user interface component executes processes that involve interaction with the patient 902, and the system interface component executes processes that modify configuration information. However, it is to be appreciated that embodiments including the update agent component 912, or any of the other components illustrated in FIG. 9, are not limited to a particular modular arrangement and other arrangements may be implemented within particular embodiments.

Computer System

As discussed above with regard to FIG. 9, various aspects and functions described herein may be implemented as specialized hardware or software components executing in one or more computer systems. There are many examples of computer systems that are currently in use. These examples include, among others, network appliances, personal computers, workstations, mainframes, networked clients, servers, media servers, application servers, database servers, and web servers. Other examples of computer systems may include mobile computing devices, such as cellular phones and personal digital assistants, and network equipment, such as load balancers, routers, and switches. Further, aspects may be located on a single computer system or may be distributed among a plurality of computer systems connected to one or more communications networks.

For example, various aspects, functions, and processes may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Consequently, embodiments are not limited to executing on any particular system or group of systems. Further, aspects, functions, and processes may be implemented in software, hardware or firmware, or any combination thereof. Thus, aspects, functions, and processes may be implemented within methods, acts, systems, system elements and components using a variety of hardware and software configurations, and examples are not limited to any particular distributed architecture, network, or communication protocol.

Figure 10:
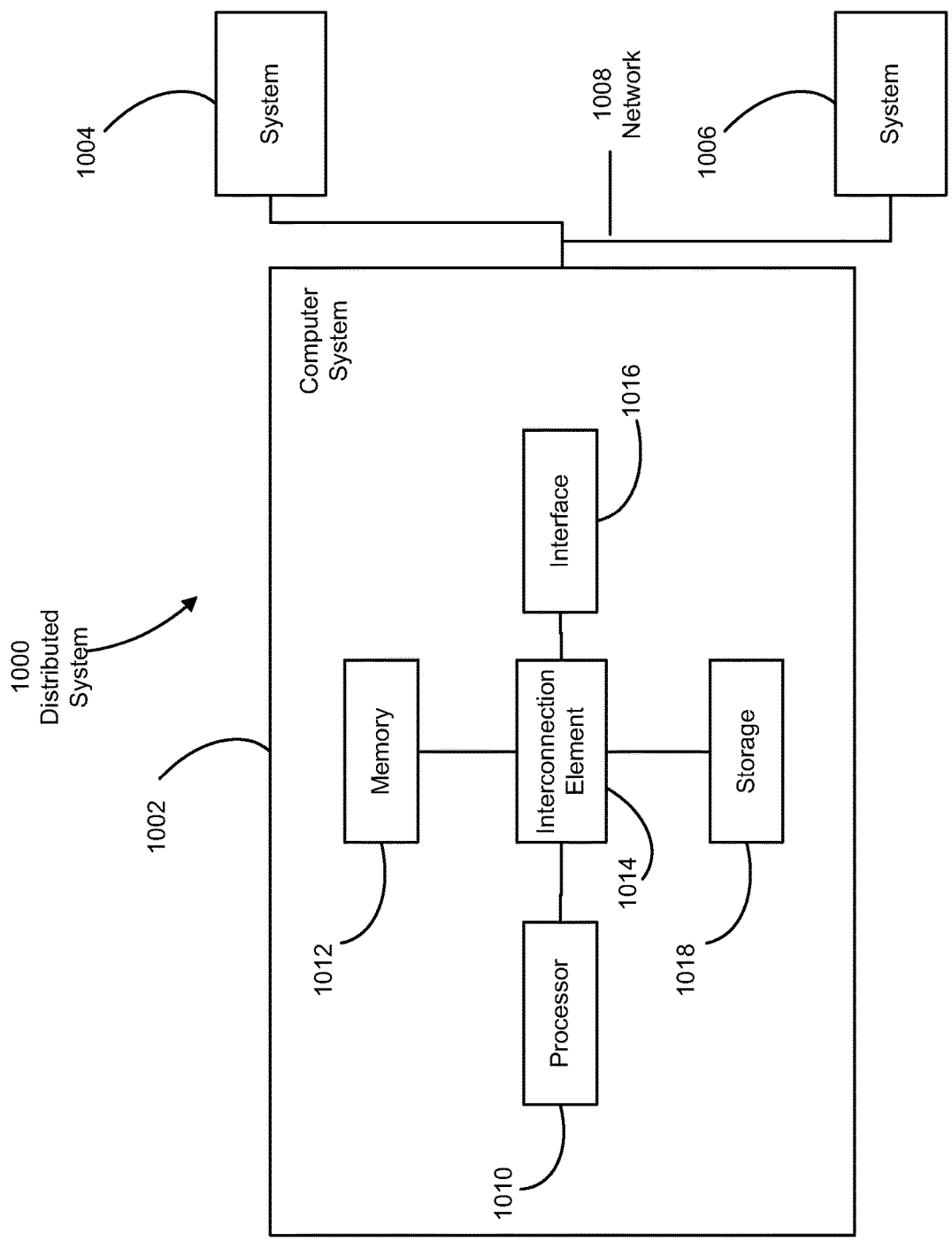
FIG. 10 is a schematic diagram of an example of a computer system that executes at least some of the processes and functions disclosed herein.

Referring to FIG. 10, there is illustrated a block diagram of a distributed computer system 1000, in which various aspects and functions are practiced. As described above with reference to FIG. 9, in at least one embodiment, the computer system 908 includes one or more distributed computer systems such as the computer system 1000. As shown in FIG. 10, the distributed computer system 1000 includes one more computer systems that exchange information. More specifically, the distributed computer system 1000 includes computer systems 1002, 1004, and 1006. As shown, the computer systems 1002, 1004, and 1006 are interconnected by, and may exchange data through, a communication network 1008. The network 1008 may include any communication network through which computer systems may exchange data. To exchange data using the network 1008, the computer systems 1002, 1004, and 1006 and the network 1008 may use various methods, protocols and standards, including, among others, Fibre Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST, and Web Services. To ensure data transfer is secure, the computer systems 1002, 1004, and 1006 may transmit data via the network 1008 using a variety of security measures including, for example, TLS, SSL, or VPN. While the distributed computer system 1000 illustrates three networked computer systems, the distributed computer system 1000 is not so limited and may include any number of computer systems and computing devices, networked using any medium and communication protocol.

As illustrated in FIG. 10, the computer system 1002 includes a processor 1010, a memory 1012, an interconnection element 1014, an interface 1016 and data storage element 1018. To implement at least some of the aspects, functions, and processes disclosed herein, the processor 1010 performs a series of instructions that result in manipulated data. The processor 1010 may be any type of processor, multiprocessor or controller. Some exemplary processors include commercially available processors such as an Intel Xeon, Itanium, Core, Celeron, or Pentium processor, an AMD Opteron processor, an Apple A4 or A5 processor, a Sun UltraSPARC or IBM Power5+ processor and an IBM mainframe chip. The processor 1010 is connected to other system components, including one or more memory devices 1012, by the interconnection element 1014.

The memory 1012 stores programs and data during operation of the computer system 1002. Thus, the memory 1012 may be a relatively high performance, volatile, random access memory such as a dynamic random access memory ("DRAM") or static memory ("SRAM"). However, the memory 1012 may include any device for storing data, such as a disk drive or other nonvolatile storage device. Various examples may organize the memory 1012 into particularized and, in some cases, unique structures to perform the functions disclosed herein. These data structures may be sized and organized to store values for particular data and types of data.

Components of the computer system 1002 are coupled by an interconnection element such as the interconnection element 1014. The interconnection element 1014 may include any communication coupling between system components such as one or more physical busses in conformance with specialized or standard computing bus technologies such as IDE, SCSI, PCI and InfiniBand. The interconnection element 1014 enables communications, such as data and instructions, to be exchanged between system components of the computer system 1002.

The computer system 1002 also includes one or more interface devices 1016 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 1002 to exchange information and to communicate with external entities, such as users and other systems.

The data storage element 1018 includes a computer readable and writeable nonvolatile, or non-transitory, data storage medium in which instructions are stored that define a program or other object that is executed by the processor 1010. The data storage element 1018 also may include information that is recorded, on or in, the medium, and that is processed by the processor 1010 during execution of the program. More specifically, the information may be stored in one or more data structures specifically configured to conserve storage space or increase data exchange performance. The instructions may be persistently stored as encoded signals, and the instructions may cause the processor 1010 to perform any of the functions described herein. The medium may, for example, be optical disk, magnetic disk or flash memory, among others. In operation, the processor 1010 or some other controller causes data to be read from the nonvolatile recording medium into another memory, such as the memory 1012, that allows for faster access to the information by the processor 1010 than does the storage medium included in the data storage element 1018. The memory may be located in the data storage element 1018 or in the memory 1012, however, the processor 1010 manipulates the data within the memory, and then copies the data to the storage medium associated with the data storage element 1018 after processing is completed. A variety of components may manage data movement between the storage medium and other memory elements and examples are not limited to particular data management components. Further, examples are not limited to a particular memory system or data storage system.

Although the computer system 1002 is shown by way of example as one type of computer system upon which various aspects and functions may be practiced, aspects and functions are not limited to being implemented on the computer system 1002 as shown in FIG. 10. Various aspects and functions may be practiced on one or more computers having a different architectures or components than that shown in FIG. 10. For instance, the computer system 1002 may include specially programmed, special-purpose hardware, such as an application-specific integrated circuit ("ASIC") tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 1002 may be a computer system including an operating system that manages at least a portion of the hardware elements included in the computer system 1002. In some examples, a processor or controller, such as the processor 1010, executes an operating system. Examples of a particular operating system that may be executed include a Windows-based operating system, such as, Windows NT, Windows 2000 (Windows ME), Windows XP, Windows Vista or Windows 7 operating systems, available from the Microsoft Corporation, a MAC OS System X operating system or an iOS operating system available from Apple Computer, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular operating system.

The processor 1010 and operating system together define a computer platform for which application programs in high-level programming languages are written. These component applications may be executable, intermediate, byte-code or interpreted code which communicates over a communication network, for example, the Internet, using a communication protocol, for example, TCP/IP. Similarly, aspects may be implemented using an object-oriented programming language, such as .Net, SmallTalk, Java, C++, Ada, C# (C-Sharp), Python, or JavaScript. Other object-oriented programming languages may also be used. Alternatively, functional, scripting, or logical programming languages may be used.

Additionally, various aspects and functions may be implemented in a non-programmed environment. For example, documents created in HTML, XML or other formats, when viewed in a window of a browser program, can render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Accordingly, the functional components disclosed herein may include a wide variety of elements (e.g., specialized hardware, executable code, data structures or objects) that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user mode application) or in a commonly shared data structure (such as an application registry that is defined by an operating system). In addition, some examples provide for both system and user interfaces that allow external entities to modify the parameters and thereby configure the behavior of the components.

Treatment Device Update Processes

Figure 11:
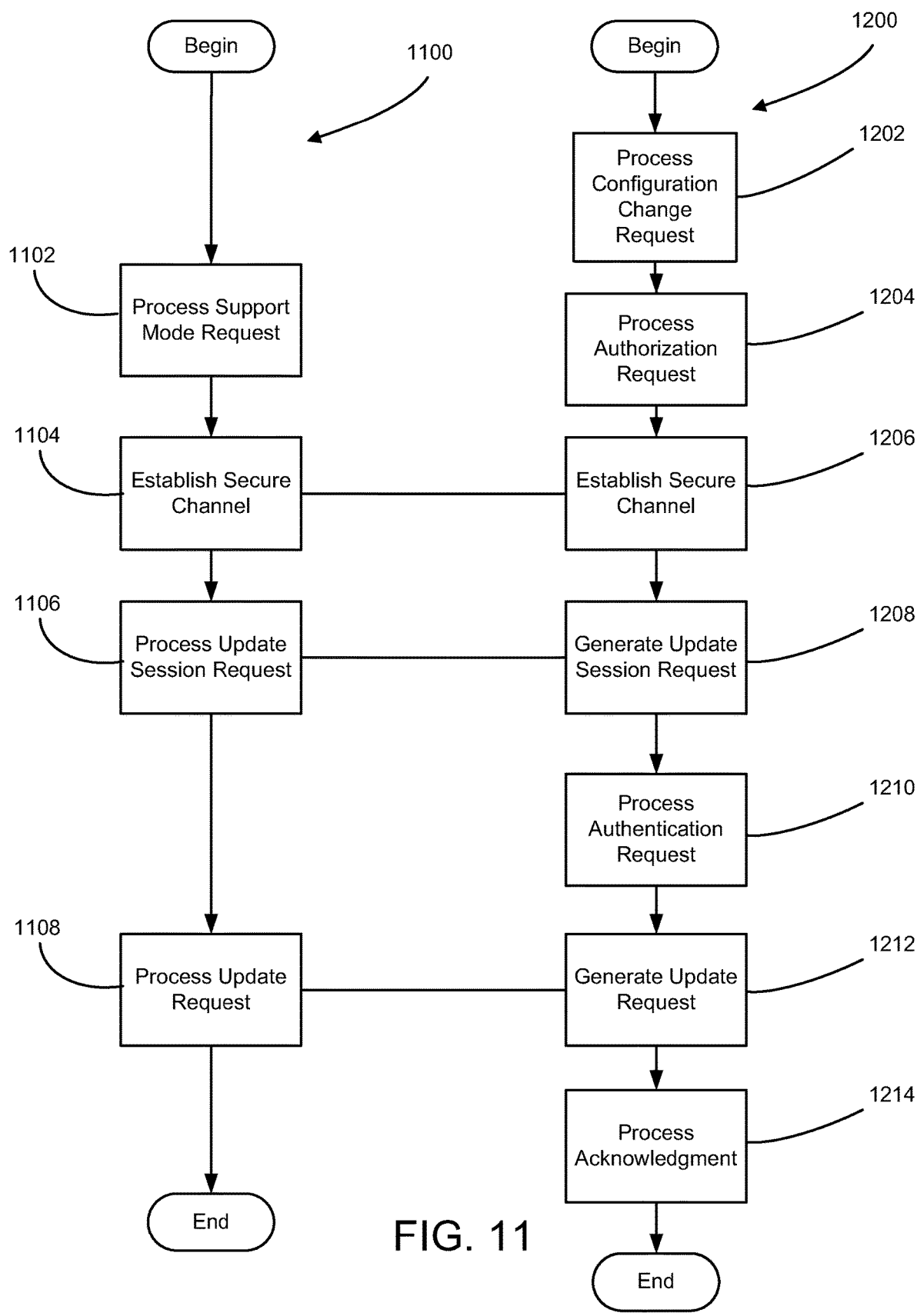
FIG. 11 is a flow diagram depicting two example processes executed to update a treatment device.

As described above with reference to FIG. 9, several embodiments perform processes that configure remote treatment devices by updating configuration information stored on the remote treatment devices via a secure communications channel. In some embodiments, these update processes are executed by a treatment device configured according to the treatment devices described above with reference to FIGS. 1-4 and 8. One example of such an update process is illustrated in FIG. 11. According to this example, the update process 1100 includes acts of processing a support mode request, establishing a secure communications channel, processing a request for an update session, and processing an update request.

In act 1102, the treatment device receives, parses, and processes a request to enter support mode (i.e., a support mode request). In at least one embodiment this request is entered by a patient, such as the patient 902 described above with reference to FIG. 9, in response to instructions communicated by a support technician, such as the support technician 904 described above with reference to FIG. 9. In some examples, the support technician communicates the instructions to the patient during a telephone conversation conducted over a voice channel, although other communication channels (e.g., email, text, and the like) may be used to communicate the instructions. In addition, in some embodiments, the treatment device itself may include one or more components through which a voice channel (or other communication channel) may be implemented.

In response to receiving and parsing the request to enter support mode, the treatment device loads and executes an update agent component, such as the update agent component described above with reference to FIG. 9. It is to be appreciated that, in some embodiments, the update agent component is only executed at the request of the patient, and is not otherwise loaded into memory or executed by the treatment device. In this way, computing resources of the treatment device are conserved, and the security of the configuration of the treatment device is enhanced.

In act 1104, the update agent component establishes a secure communications channel with an update control component, such as the update control component 914 described above with reference to FIG. 9, via a network, such as the network 910 described above with reference to FIG. 9. This communications channel may be secured by any security technology known, such as by an encrypted VPN implemented using wireless or wired data communications or the like.

In act 1106, the update agent component processes a request for an update session (i.e., an update session request). In one embodiment, the update agent component receives the request via execution of act 1208 by the update control component, parses the request, and transmits an acknowledgment to the update control component in response to receiving and successfully parsing the request. Also in this embodiment, the update agent component generates and displays a random code to be used as an update session identifier on a display (e.g., of the treatment device) in response to receiving and parsing the request. In another embodiment, the update agent component prompts the patient to enter an update session identifier in response to receiving and parsing the request. In still another embodiment, the update agent component generates the update session identifier and provides the update session identifier to the patient via a different communication channel, such as via audio, email or text message. In yet another embodiment, the update agent component generates the update session identifier and transmits the update session identifier to the update control component in response to receiving and parsing the update session request. The update agent component may further present a prompt on the display that instructs the patient to provide the update session identifier to the support technician.

In act 1108, the update agent component processes a request to update configuration information of the treatment device (i.e., an update session request). In one embodiment, the update agent component receives the request via execution of act 1212 by the update control component. In response to receiving the request, the update agent component decodes the request and validates the decoded request. In some embodiments decoding the request includes decrypting the request using SHA-2 or some other strong encryption process.

In at least one embodiment, the update agent component validates the decoded request by detecting whether a unique device identifier (e.g., serial number) stored in the memory of the treatment device matches (e.g., is equal to) a unique identifier of the device included in the decoded request. In another embodiment, the update agent component validates the decoded request by detecting whether a unique patient identifier (e.g., name, social security number, insurance account number, or biometric identifier, such as ECG signal, heart rate variability, heart rate trends, activity trends, body position trends, heart walk results, health survey information, voice, and the like) stored in the memory of the treatment device matches (e.g., is equal to) a unique identifier that of the patient included in the decoded request. In another embodiment, the update agent component validates the decoded request by detecting whether a previous generated and active update session identifier (e.g., randomly generated number) matches (e.g., is equal to) a unique identifier that of the device included in the decoded request.

Also within the act 1108, responsive to validating the decoded request, the update agent component reconfigures the treatment device by applying the device update information to the configuration information of the treatment device. In some embodiments, the device update information is applied to the configuration information by storing the device update information within the configuration information or by adjusting the configuration information using the device update information. In at least one embodiment, in response to successfully applying (or failing to apply) the device update information, the update agent component displays an update code (also referred to herein as an acknowledgement code) on a display (e.g., of the treatment device). The acknowledgement code indicates success or failure of the update process. In another embodiment, the update agent component also transmits a message including the acknowledgement code to the update control component.

In some embodiments, if the update agent component is unable to either decode or validate the request, the update agent component displays an error message. In at least one embodiment, if the update agent component is unable to successfully apply the device update information to the treatment device, the update agent component rolls back any changes made to the configuration information of the treatment device and displays an error message. After completion of the act 1108, the update agent component terminates the process 1100.

Processes in accord with the process 1100 enable treatment devices to process updates to configuration information is a highly secure and reliable manner.

As described above with reference to FIG. 9, several embodiments perform processes that update configuration information of treatment devices. In some embodiments, these update processes are executed by a computer system configured according to the computer systems described above with reference to FIG. 10. One example of such an update process is illustrated in FIG. 11. According to this example, the update process 1200 includes acts of processing a request to change configuration information of the treatment device, processing a request for authorization, establishing a secure communications channel, generating an update session request, processing a request for authentication, generating an update request, and processing an acknowledgement.

In act 1202, an update control component, such as the update control component 914 described above with reference to FIG. 9, processes a request to change the configuration information for a treatment device (i.e., a configuration change request). In at least one embodiment, the update control component receives this request from a support technician, such as the support technician 904 described above with reference to FIG. 9. The request may include information that identifies the patient and that is descriptive of parameters to be altered and information to be gathered. In response to receiving the request, the update control component parses the request and stores the configuration information included in the request for subsequent processing.

In act 1204, the update control component processes a request for authorization. In one embodiment, the update control component receives this request from the support technician or a supervisor of the support technician who is attempting to apply the changes to the configuration information made in the act 1202 above. This request may include information descriptive of authorization credentials of a person authorized to approve of configuration changes to the treatment device. In response to receiving this request, the update control component parses the request and attempts to verify that authorization credentials included in the request are valid (e.g., match previously stored credentials of a person recorded as being authorized to effect changes to treatment devices). If the credentials are verified, the update control component proceeds to act 1206. Otherwise, the update control component displays an error message and displays a prompt to repeat the authorization request.

In the act 1206, the update control component establishes a secure communications channel with an update agent component, such as the update agent component 912 described above with reference to FIG. 9, via a network, such as the network 910 described above with reference to FIG. 9. This communications channel may be secured by any security technology known, such as by an encrypted VPN implemented using wireless or wired data communications or the like. In the act 1208, the update control component generates a request for an update session (i.e., an update session request) and transmits the request to the update agent component.

In the act 1210, the update control component processes a request to authenticate the update session (i.e., an authentication request). In one embodiment, the update control component receives this request from the support technician, who enters the request after speaking with the patient to determine the update session identifier generated by the update agent component in the act 1106. In another embodiment, the update control component receives this request in two phases. In the first phase, the support technician enters the request and submits the request to a supervisor for approval. In the second phase, the supervisor logs in and approves the request. In still another embodiment, the update control component receives the request directly from the update agent component and the support technician reviews and approves of, or rejects, the request. The request may include the update session identifier generated by the update agent component as received from the update agent component or as entered into the update control component by the support technician. In response to receiving this request, the update control component parses the request and stores, in memory for subsequent processing, the update session identifier included in the request.

In the act 1212, the update control component generates, encodes, and transmits an update request to the update agent component. The request may include device update information descriptive of changes to parameters of the treatment device or information to be gathered via the treatment device. The request may also include the identifier of the update session, a unique identifier of the treatment device, a unique identifier of the patient, time and date information, and the like. In at least one embodiment, the update control component encodes the request by encrypting the request.

In act 1214, the update control component processes an acknowledgment code generated and displayed by the update agent component. In one embodiment, the acknowledgment code is entered by the support technician, who enters the acknowledgment code after speaking with the patient to determine the acknowledgment code generated by the update agent component in the act 1108. The acknowledgment code may indicate successful application of the update device information, in which case no further action is required, or failure to properly apply the update device information, in which case the support technician may take further steps to reset the configuration information of the treatment device, conduct another update session, or take some other corrective action. After completion of the act 1214, the computer system terminates the process 1200.

Processes in accord with the process 1200 enable computer systems to drive highly secure and reliable update processes for remote treatment devices.

Figure 12:
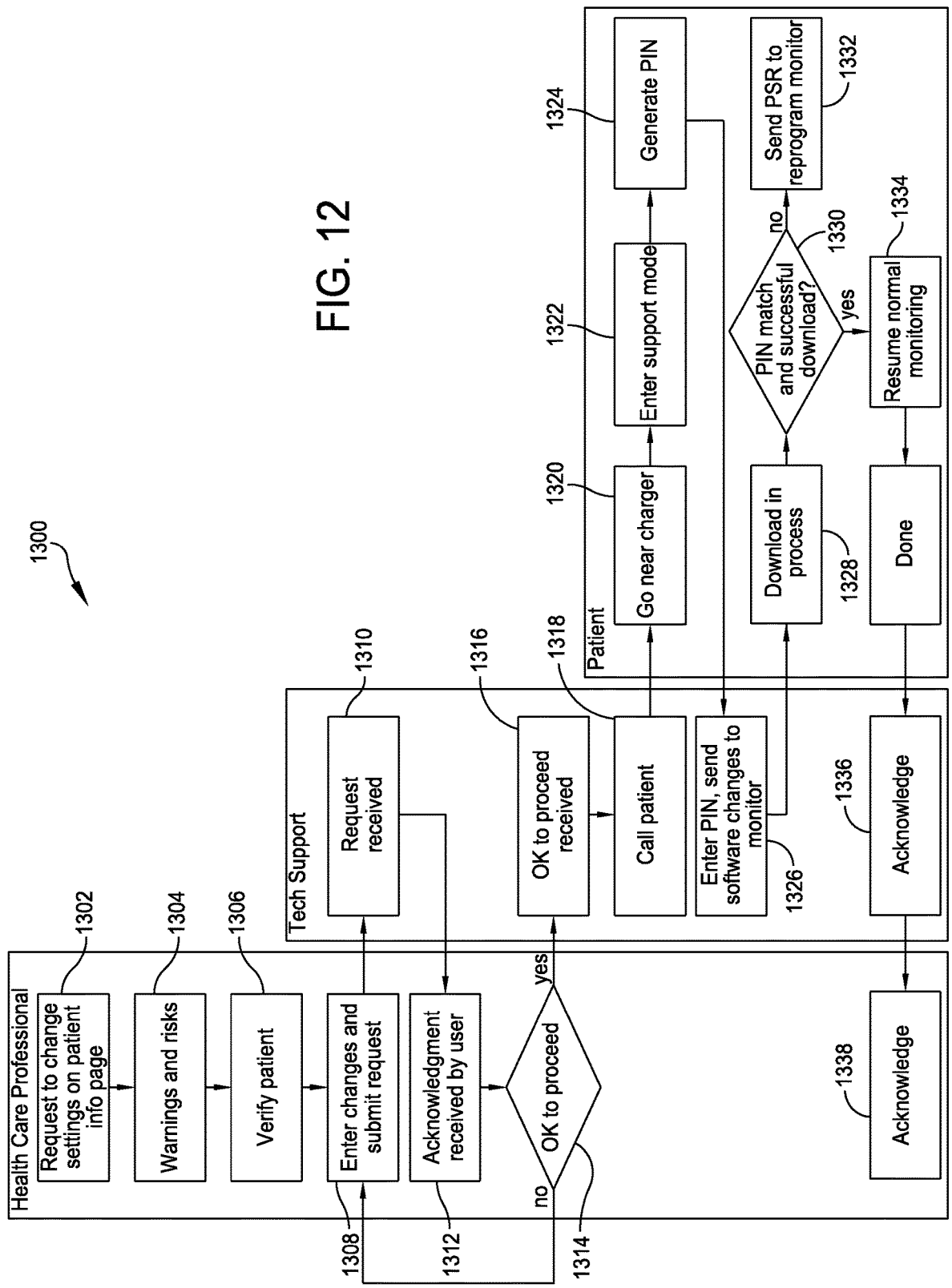
FIG. 12 is a flowchart depicting an exemplary method of configuring or reconfiguring a remote device, such as a wearable medical monitoring and/or treatment device in accordance with an aspect of the present invention.

FIG. 12 is a flowchart depicting an exemplary update process 1300 that configures or reconfigures a treatment device, such as the treatment device 906 described above with reference to FIG. 9. As illustrated in FIG. 12, the update process 1300 includes several acts that are described further below.

As used in FIGS. 12-15, "PSR" refers to a patient support representative who visits patients and assists them in configuring or re-configuring the wearable medical monitoring and/or treatment device. PIN refers to the unique random code generated by the treatment device as the update session identifier. The term "monitor" generally refers to the monitor 130 associated with the wearable device 100. The term "charger" generally refers to the base unit 830 of FIG. 8.

In act 1302, a user interface provided by a web portal component, such as the web portal component 916 described above with reference to FIG. 9, receives a request to alter the configuration of a treatment device, such as the treatment device 906 described above with reference to FIG. 9, fitted to an identified patient, such as the patient 902 described above with reference to FIG. 9. The request may be entered into the user interface by an authenticated web portal user, such the health care professional 918 described above with reference to FIG. 9 (e.g., a doctor of the identified patient). One example a screen included in the user interface is described further below with reference to FIG. 15.

In act 1304, the user interface displays risks and warnings associated with the altered configuration and receives an indication to proceed from the user. In act 1306, the user interface displays patient data for verification and receives an indication to proceed from the user. In act 1308, the user interface receives an instruction to submit the requested altered configuration.

In act 1310, a support interface, such as the support interface described above with reference to FIG. 9, receives a configuration change request for the treatment device. This request may be entered by a support technician, such as the support technician described above with reference to FIG. 9. Also as part of the act 1310, the support interface transmits an acknowledgment to the user interface of the web portal component 916.

In act 1312, the user interface displays an indication that the request to alter the configuration of the treatment device has been received and entered. In the act 1312, the user interface further prompts the user to enter an indication as to whether to proceed with the configuration process. If the indication to proceed is entered, the user interface transmits an instruction to proceed to the support interface, in the act 1314.

In act 1316, the support interface displays an indication that the web portal user has confirmed that the configuration process should continue. In act 1318, the support technician calls the patient and instructs the patient to go near a base unit, such as the base unit 830 described above with reference to FIG. 8, enter a support mode request for the treatment device to enter support mode, and generate a update session identifier (e.g., PIN). In embodiments where the treatment device includes components configured to communicate with the support interface without the use of the base unit (e.g., cellular communication components, WiFi components, and the like), the instruction to go near the base unit may be omitted.

In act 1320, the patient moves near the base unit. In act 1322, the patient enters a support mode request. In response to receiving and parsing the request, the treatment device enters support mode. In act 1324, the patient enters an update session request to generate an update session identifier into the treatment device. In response to receiving and parsing the request to generate an update session identifier, the treatment device generates and displays the update session identifier.

In act 1326, the patient communicates the update session identifier to the support technician who enters the update session identifier into the support interface. The support interface receives the update session identifier and an indication to proceed with the update process. In response to this indication, the support interface generates, encodes, and transmits an update request including the update session identifier to the treatment device.

In act 1328, the treatment device displays an indication that a download is in process. In act 1330, the treatment device receives the encoded request, decodes the request, and attempts to validate the request. In this embodiment, the treatment device validates the request at least in part by verifying that the update session identifier in the request matches (e.g., equals) the update session identifier generated in the act 1324. If the treatment device is unable to validate the request, the treatment device transmits a service request to the support interface in act 1332. Otherwise, in act 1334 the treatment device applies the changes to its configuration, transmits an acknowledgment to the support interface, and resumes normal operation under the new configuration.

In act 1336, the support interface receives the acknowledgment from the treatment device, displays an indication of success or failure of the update process, and transmits an acknowledgement to the user interface of the web portal component. In act 1338, the user interface of the web portal component displays an indication of success or failure of the update process and the update process 1300 ends.

FIG. 13 is pictorial representation of certain screens and other elements that may be displayed on a display of a monitor of the treatment device. These user interface elements may be displayed during the execution of update processes such as the update process 1300 described above with reference to FIG. 12 or the update process 1100 described above with reference to FIG. 11.

FIG. 13 illustrates a home screen 1400, a main menu screen 1402, a settings screen 1404, a confirmation screen 1406, a transition screen 1408, an update code screen 1410, a support PIN screen 1412, a progress screen 1414, and a confirmation screen 1416. In one embodiment, the treatment device is configured to utilize these elements as follows.

The treatment device displays the home screen 1400 by default. In response to detecting a selection of the menu tab 1418, the treatment device displays the main menu screen 1402. In response to detecting a selection of the settings button 1420, the treatment device displays the settings screen 1404. In response to detecting a selection of the support mode button 1422, the treatment device displays the confirmation screen 1406. In response to detecting a selection of the ok button 1424, the treatment device displays the transition screen 1408 and attempts to establish a secure communications channel with an update control component, such as the update control component 914 describe above with reference to FIG. 9.

If the treatment device encounters a problem in establishing the secure communications channel, the treatment device displays the update code screen 1410. A patient, such as the patient 902 described above with reference to FIG. 9, conducting an update process may provide the update code to a support technician, such as the support technician 904 described above with reference to FIG. 9, for further information regarding the problem and potential actions to correct the problem. If the treatment device successfully establishes the secure communication channel, the treatment device displays the support PIN screen 1412.

The patient may provide the PIN (i.e., the update session identifier) to the support technician. The support technician enters the PIN into the support interface executing on the computer system 908. The update control component executing on the computer system 908 generates, encodes, and transmits an update request to the treatment device. As illustrated in FIG. 13, the transmission is routed through the base unit 830. However, in examples where the treatment device can communicate with the Internet independently of the base unit 830, the transmission is routed to the treatment device without passing through the base unit 830. In any case, the treatment device may display the progress screen 1414 while downloading and processing the update request.

Responsive to receiving, decoding, and validating the update request, the treatment device applies the device update information included in the request to the configuration information of the treatment device. If any problems are encountered while applying the device update information, the treatment device rolls back any changes made and records information descriptive of the problem for subsequent processing.

Next, the treatment device displays the confirmation screen 1416. The patient may provide the update code displayed in the confirmation screen 1416 to the support technician. The support technician enters the update code into the support interface. The support interface then displays an indication of success or failure of the update process based on the value of the update code. If the update process failed, the support technician may schedule a subsequent visit to the patient to apply the update. In response to detecting a selection of the ok button 1426, the treatment device displays the home screen 1400.

Processes 1100-1400 each depict one particular sequence of acts in a particular embodiment. The acts included in these processes may be performed by, or using, one or more computer systems or treatment devices specially configured as discussed herein. Some acts are optional and, as such, may be omitted in accord with one or more embodiments. Additionally, the order of acts can be altered, or other acts can be added, without departing from the scope of the embodiments described herein. Furthermore, as described above, in at least one embodiment, the acts are performed on particular, specially configured machines, namely a device update system configured according to the examples and embodiments disclosed herein.

FIG. 14 is an illustration of a user interface screen 1500 that may be displayed to permit remote configuration or reconfiguration of a treatment device. In some embodiments, this screen is displayed by the treatment device. In other embodiments, this screen is served by a web portal component, such as the web portal component 916 described above with reference to FIG. 9, to a browser executing on a computer system, such as the computer system 920 described above with reference to FIG. 9. The user interface screen 1500 includes patient information section 1502, treatment device information section 1504, change request link 1506, and submit request button 1508. The patient information section 1502 displays basic patient information such as name, identifier, and status. The treatment device information section 1504 displays basic treatment device information such as model, serial number, date last used, and additional information, such as a version number of one or more components of the treatment device. The change request link 1506 is a link to a user interface screen configured to receive information descriptive of a request to alter the configuration of a treatment device. The submit request button 1508 generates an update configuration request to be transmitted to a support technician for implementation via a configuration or update process.

FIG. 15 is an illustration of a user interface screen 1600 that may be displayed on a computer display screen used by a support technician to reconfigure a wearable medical monitoring and/or treatment device remotely. The user interface screen 1600 includes patient information section 1602, treatment device parameters section 1604, action combobox 1606, PIN text box 1608, process code text box 1610, go button 1612, and reset configuration button 1614. The patient information section 1602 displays patient information such as name, identifier, address, date of birth, center code, and treatment device serial number. The treatment device parameters section 1604 displays adjustable treatment device parameters such as VT rate threshold, VT response time, VF rate threshold, VF response time, patient sleep interval start time, patient sleep interval end time, response time extension used during the sleep interval, and the amounts of energy to be used in treatments 1-5. The action combobox 1606 displays the action that will be executed if the support interface detects a selection of the go button 1612. The PIN text box displays the currently entered PIN. The process code text box 1610 displays the currently entered update code.

Usage Scenario

According to one particular example, a physician initiates an update process to the configuration of a treatment device utilizing the embodiments disclosed herein. According to this example, the physician sends a message through a secure telecommunications network, such as the web portal component 916 described above with reference to FIG. 9, to a support technician, such as the support technician 904 described above with reference to FIG. 9. The support technician accesses a support interface, such as the support interface described above with reference to FIGS. 14 and 15. The support interface displays information about a patient, such as the patient 902 described above with reference to FIG. 9. This information may include the name, date of birth, and condition. The support technician enters the selections as instructed by the physician. In response to receiving and parsing the selections, the support interface displays pop-ups that report the risks of the selections.

Once the physician confirms the change, the support technician calls the patient. The support technician informs the patient of the physician request and, where a base unit is used in the update process, the support technician asks the patient to move within range of the base unit of the treatment device. The support technician next provides step by step instructions for the patient to complete a support mode request.

In response to receiving the support mode request, the treatment device enters support mode and attempts to establish a secure communication channel with the computer system executing the support interface. If the attempt to establish the secure communication channel times out or otherwise fails, the treatment device returns to the main screen if no further action is taken. Otherwise, the treatment device generates and displays a random code that identifies the active update session and prompts the patient to provide the random code to the support technician.

The patient provides the random code to the support technician who enters the random code into the support interface. The support interface generates an update request that includes the following information: serial number, an identifier of the patient (name or ID stream) date and time of the request, the random code, changes to the configuration information of the treatment device (current setting of a parameter and a change for the parameter). In this example, an ID stream includes a uniquely encoded ID string that identifies the patient. The string may contain a center code that identifies data routing back to the physician, patient name and date time stamp of setup. The support interface next encodes the update request using a private SSH encryption key and downloads the encoded update request to the treatment device.

The treatment device decodes the encoded update request using a public SSH decryption key and validates the update request using local information descriptive of the serial number, patient identifier, and update session identifier (e.g., random code). If the update request is valid, the treatment device updates its configuration in accord with the device update information included in the update request. If the update request is not valid, the treatment device aborts the update process. Next, the treatment device generates and transmits an acknowledgment message that includes information indicating the success or failure of the update process. Responsive to receiving the acknowledgement, the support interface stores an audit trail of all activity that occurred during the update process. The audit trail is available to the physician from the web portal component via a web-browser and an Internet connection.

The support technician remains on the phone with the patient until the treatment device indicates success or failure of the update process. If the update process is successful, the support technician instructs the patient to cycle power to the treatment device.

It is to be appreciated that any sort of configuration information may be downloaded and applied to the treatment device using the embodiments disclosed herein. For instance, in another example, a support technician conducts an update of the software or firmware of the treatment device. In this example, the methods and systems disclosed herein are utilized to download the software or firmware update, validate the update, and apply the update. In addition, it is to be appreciated that, in some instances, technical support personnel may conduct both the sides of the update process (i.e., perform the actions of the patient 902 as well as the actions of the support technician 904).

Having now described some illustrative embodiments of the invention, it should be apparent to those skilled in the art that the foregoing is illustrative and not limiting, having been presented by way of example. In particular, although many of the examples presented herein involve specific combinations of method acts or system elements, it is understood that those acts and those elements may be combined in other ways to accomplish the same objectives. Acts, elements and features discussed only in connection with one embodiment are not intended to be excluded from a similar role in other embodiments.

Note that in the Figures, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. The program storage medium includes data signals embodied in one or more of a computer disk (magnetic, or optical (e.g., CD or DVD, or both)), non-volatile memory, tape, a system memory, and a computer hard drive.

From the foregoing, it will be appreciated that the wearable treatment device described herein is worn by the subject and senses information about the subject's activity, wellness, and quality of life via direct sensing or user provided data entries. The treatment device can determine if treatment is needed based on the subject's physical condition, can adjust treatment regiments based on sensed information, and can apply treatment to the subject as necessary. The wearable treatment device can gather information about the subject's health in real time over a substantially continuous period. This information can be aggregated to form a comprehensive medical history of the subject, which can be used to determine if past treatment regimens are successful and if modifications should be made.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects and embodiments disclosed herein.

Publications, patents, and patent documents referred to in this document are incorporated by reference herein in their entirety, as though individually incorporated by reference. In the event of inconsistent usages between this document and those documents so incorporated by reference, the usage in the incorporated references is supplementary to that of this document; for irreconcilable inconsistencies, the usage in this document controls.

References to "or" may be construed as inclusive, so that any terms described using "or" may indicate any of a single, more than one, and all of the described terms.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A system configured to update remote medical devices, the system comprising:
 a memory storing device update information specifying one or more patient settings of an ambulatory medical treatment device configured to be worn by a patient and to provide a treatment protocol to the patient if the patient experiences a cardiac arrhythmia event treatable by one or more therapy shocks to be delivered to the patient during provision of the treatment protocol,
 wherein the one or more patient settings comprise rate threshold information for identifying the cardiac arrhythmia event and energy setting information for the one or more therapy shocks to be delivered to the patient during provision of the treatment protocol if the patient experiences the cardiac arrhythmia event, the treatment protocol comprising applying the one or more therapy shocks to the patient if the patient experiences the cardiac arrhythmia event;
a network interface; and
at least one processor coupled to the memory and the network interface and configured to
receive a configuration change request to update the one or more patient settings of the ambulatory medical treatment device, the one or more patient settings defining at least a portion of the treatment protocol to be provided to the patient when the patient experiences the cardiac arrhythmia event,
receive an authorization request comprising authorization credentials for authorizing one or more updates to the one or more patient settings of the ambulatory medical treatment device,
verify the authorization credentials in the authorization request,
establish a secure communication channel with the ambulatory medical treatment device via the network interface in response to verification of the authorization credentials,
receive an authentication request comprising an identifier of an update session,
generate a configuration update request comprising
one or more updates to the one or more patient settings of the ambulatory medical treatment device, thereby defining an updated treatment protocol to be provided to the patient by the ambulatory medical treatment device if the patient experiences the cardiac arrhythmia event treatable by the one or more therapy shocks, and
the identifier of the update session,
encode the configuration update request to generate an encoded configuration update request,
transmit the encoded configuration update request to the ambulatory medical treatment device via the secure communication channel, and
receive an acknowledgement code from the ambulatory medical treatment device, the acknowledgement code comprising an indication that the ambulatory medical treatment device successfully applied the one or more updates to the one or more patient settings of the ambulatory medical treatment device so that the ambulatory medical treatment device operates according to the one or more updates to the one or more patient settings of the ambulatory medical treatment device to provide the updated treatment protocol to the patient if the patient experiences the cardiac arrhythmia event treatable by the one or more therapy shocks.

2. The system according to claim 1, wherein the at least one processor is configured to encode the configuration update request at least in part by encrypting the configuration update request.

3. The system of claim 1, wherein the one or more updates to the one or more patient settings of the ambulatory medical treatment device further comprise information descriptive of device settings to be applied to the ambulatory medical treatment device.

4. The system of claim 1, wherein the memory further stores a device identifier that uniquely identifies the ambulatory medical treatment device and the configuration update request further comprises the device identifier of the ambulatory medical treatment device.

5. The system of claim 1, wherein the memory further stores a patient identifier that uniquely identifies a patient assigned to the ambulatory medical treatment device and the configuration update request further comprises the patient identifier.

6. The system of claim 5, wherein the patient identifier comprises a biometric identifier that is unique to the patient.

7. The system of claim 1, further comprising the ambulatory medical treatment device.

8. The system of claim 7, wherein the ambulatory medical treatment device comprises
a device memory storing configuration information specifying at one or more patient settings of the ambulatory medical treatment device;
a treatment component configured to deliver the one or more therapy shocks to the patient during provision of the treatment protocol;
one or more processors coupled to the device memory and the treatment component and configured to operate the ambulatory medical treatment device as specified by the configuration information;
a user interface component executable by the one or more processors and configured to
receive a request to initiate an update session, and
generate an update session identifier responsive to receiving the request to initiate the update session; and
a system interface component executable by the one or more processors and configured to
receive the encoded configuration update request comprising an identifier of the update session and the one or more updates to the one or more patient settings of the ambulatory medical treatment device;
decode the encoded configuration update request to generate a decoded configuration update request comprising the one or more updates to the one or more patient settings of the ambulatory medical treatment device and the identifier of the update session;
validate the decoded configuration update request at least in part by determining that the update session identifier matches the identifier of the update session comprised in the decoded configuration update request; and
apply, in response to validating the decoded configuration update request, the one or more updates to the one or more patient settings of the ambulatory medical treatment device to the configuration information, thereby altering the one or more patient settings of the ambulatory medical treatment device.

9. The system of claim 8, wherein the system interface component is configured to decode the encoded configuration update request at least in part by decrypting the encoded configuration update request.

10. The system of claim 8, wherein the system interface component is further configured to:
detect at least one of success and failure of the update session; and
rollback any of the one or more updates to the one or more patient settings of the ambulatory medical treatment device applied in response to failure of the update session.

11. The system of claim 8, further comprising a display coupled to the one or more processors, wherein the user interface component is further configured to:
display the update session identifier on the display; and
display an indication of at least one of success and failure of the update session on the display.

12. The system of claim 10, wherein the device memory further stores a unique identifier of the ambulatory medical treatment device, the encoded configuration update request comprises a device identifier of the ambulatory medical treatment device, and the system interface component is configured to validate the decoded configuration update request at least in part by determining that the device identifier of the ambulatory medical treatment device comprised in the decoded configuration update request matches the unique identifier of the ambulatory medical treatment device stored in the device memory.

13. The system of claim 12, wherein the device memory further stores a unique identifier of the patient, the encoded configuration update request further comprises a patient identifier of the patient, and the system interface component is configured to further validate the decoded configuration update request at least in part by determining that the patient identifier comprised in the decoded configuration update request matches the unique identifier of the patient stored in the device memory.

14. The system of claim 13, wherein the patient identifier comprised in the decoded configuration update request and the unique identifier of the patient stored in the device memory comprise biometric identifiers.

15. A method to update remote medical devices executed by a computer system comprising a memory, a network interface, and at least one processor coupled to the memory and the network interface, the memory storing device update information specifying one or more patient settings of an ambulatory medical treatment device configured to be worn by a patient and to provide a treatment protocol to the patient if the patient experiences a cardiac arrhythmia event, the method comprising:
receiving, by the at least one processor, a configuration change request to update the one or more patient settings of the ambulatory medical treatment device, the one or more patient settings defining at least a portion of the treatment protocol to be provided to the patient if the patient experiences a cardiac arrhythmia event treatable by one or more therapy shocks to be delivered to the patient during provision of the treatment protocol, wherein the one or more patient settings comprise rate threshold information for identifying the cardiac arrhythmia event and energy setting information for the one or more therapy shocks to be delivered to the patient during provision of the treatment protocol if the patient experiences the cardiac arrhythmia event, the treatment protocol comprising applying the one or more therapy shocks to the patient if the patient experiences the cardiac arrhythmia event;
receiving, by the at least one processor, an authorization request comprising authorization credentials for authorizing one or more updates to the one or more patient settings of the ambulatory medical treatment device;
verifying, by the at least one processor, the authorization credentials in the authorization request;
establishing, by the at least one processor, a secure communication channel with the ambulatory medical treatment device via the network interface in response to verification of the authorization credentials;
receiving, by the at least one processor, an authentication request comprising an identifier of an update session;
generating, by the at least one processor, a configuration update request comprising
one or more updates to the one or more patient settings of the ambulatory medical treatment device, thereby defining an updated treatment protocol to be provided to the patient by the ambulatory medical treatment device if the patient experiences the cardiac arrhythmia event treatable by the one or more therapy shocks, and
the identifier of the update session;
encoding, by the at least one processor, the configuration update request to generate an encoded configuration update request;
transmitting, by the at least one processor, the encoded configuration update request to the ambulatory medical treatment device via the secure communication channel; and
receiving, by the at least one processor, an acknowledgement code from the ambulatory medical treatment device, the acknowledgement code comprising an indication that the ambulatory medical treatment device successfully applied the one or more updates to the one or more patient settings of the ambulatory medical treatment device so that the ambulatory medical treatment device operates according to the one or more updates to the one or more patient settings of the ambulatory medical treatment device to provide the updated treatment protocol to the patient if the patient experiences the cardiac arrhythmia event treatable by the one or more therapy shocks.

16. The method of claim 15, further comprising:
receiving, by the ambulatory medical treatment device, a request to initiate an update session;
generating, by the ambulatory medical treatment device, an update session identifier responsive to receiving the request to initiate the update session;
receiving, by the ambulatory medical treatment device, the encoded configuration update request comprising an identifier of the update session and the one or more updates to the one or more patient settings of the ambulatory medical treatment device;
decoding, by the ambulatory medical treatment device, the encoded configuration update request to generate a decoded configuration update request comprising the one or more updates to the one or more patient settings of the ambulatory medical treatment device and the identifier of the update session;
validating, by the ambulatory medical treatment device, the decoded configuration update request at least in part by determining that the update session identifier matches the identifier of the update session comprised in the decoded configuration update request; and
applying, by the ambulatory medical treatment device in response to validating the decoded configuration update request, the one or more updates to the one or more patient settings of the ambulatory medical treatment device to configuration information, thereby altering the one or more patient settings of the ambulatory medical treatment device.

17. The method of claim 15, wherein generating the configuration update request comprises storing a device identifier that uniquely identifies the ambulatory medical treatment device within the configuration update request.

18. The method of claim 15, wherein generating the configuration update request comprises storing a patient identifier that uniquely identifies a patient assigned to the ambulatory medical treatment device within the configuration update request.

19. A non-transitory computer readable medium specifying one or more patient settings of an ambulatory medical treatment device configured to be worn by a patient and to provide a treatment protocol to the patient if the patient experiences a cardiac arrhythmia event, the non-transitory computer readable medium encoded with instructions executable by at least one processor to implement a process to update remote medical devices, the process comprising:

receiving a configuration change request to update the one or more patient settings of the ambulatory medical treatment device, the one or more patient settings defining at least a portion of the treatment protocol to be provided to the patient if the patient experiences a cardiac arrhythmia event treatable by one or more therapy shocks to be delivered to the patient during provision of the treatment protocol, wherein the one or more patient settings comprise rate threshold information for identifying the cardiac arrhythmia event and energy setting information for the one or more therapy shocks to be delivered to the patient during provision of the treatment protocol if the patient experiences the cardiac arrhythmia event, the treatment protocol comprising applying the one or more therapy shocks to the patient if the patient experiences the cardiac arrhythmia event;

receiving an authorization request comprising authorization credentials for authorizing one or more updates to the one or more patient settings of the ambulatory medical treatment device;

verifying the authorization credentials in the authorization request;

establishing a secure communication channel with the ambulatory medical treatment device via a network interface in response to verification of the authorization credentials;

receiving an authentication request comprising an identifier of an update session;

generating a configuration update request comprising
one or more updates to the one or more patient settings of the ambulatory medical treatment device, thereby defining an updated treatment protocol to be provided to the patient by the ambulatory medical treatment device if the patient experiences the cardiac arrhythmia event treatable by the one or more therapy shocks, and
the identifier of the update session;

encoding the configuration update request to generate an encoded configuration update request;

transmitting the encoded configuration update request to the ambulatory medical treatment device via the secure communication channel; and receiving an acknowledgement code from the ambulatory medical treatment device, the acknowledgement code comprising an indication that the ambulatory medical treatment device successfully applied the one or more updates to the one or more patient settings of the ambulatory medical treatment device so that the ambulatory medical treatment device operates according to the one or more updates to the one or more patient settings of the ambulatory medical treatment device to provide the updated treatment protocol to the patient if the patient experiences the cardiac arrhythmia event treatable by the one or more therapy shocks.

20. The computer readable medium of claim 19, wherein generating the configuration update request comprises storing a device identifier that uniquely identifies the ambulatory medical treatment device within the configuration update request.

21. The system of claim 1, wherein the cardiac arrhythmia event comprises at least one of a defibrillation event and a pacing event.

22. The system of claim 21, wherein the defibrillation event comprises at least one of a ventricular tachycardia event and a ventricular fibrillation event, and the pacing event comprises a bradycardia event.

23. The system of claim 1, wherein the one or more updates to the one or more patient settings of the ambulatory medical treatment device further comprise updates to one or more of the rate threshold information for identifying the cardiac arrhythmia event and the energy setting information for the one or more therapy shocks to be delivered to the patient during provision of the treatment protocol.

24. The method of claim 15, wherein the cardiac arrhythmia event comprises at least one of a defibrillation event and a pacing event.

25. The method of claim 24, wherein the defibrillation event comprises at least one of a ventricular tachycardia event and a ventricular fibrillation event, and the pacing event comprises a bradycardia event.

26. The method of claim 15, wherein the one or more updates to the one or more patient settings of the ambulatory medical treatment device further comprise updates to one or more of the rate threshold information for identifying the cardiac arrhythmia event and the energy setting information for the one or more therapy shocks to be delivered to the patient during provision of the treatment protocol.

27. The computer readable medium of claim 19, wherein the cardiac arrhythmia event comprises at least one of a defibrillation event and a pacing event.

28. The computer readable medium of claim 27, wherein the defibrillation event comprises at least one of a ventricular tachycardia event and a ventricular fibrillation event and the pacing event comprises a bradycardia event.

29. The computer readable medium of claim 19, wherein the one or more updates to the one or more patient settings of the ambulatory medical treatment device further comprise updates to one or more of the rate threshold information for identifying the cardiac arrhythmia event and the energy setting information for the one or more therapy shocks to be delivered to the patient during provision of the treatment protocol.

* * * * *